(12) United States Patent
Gunasekera et al.

(10) Patent No.: US 6,495,594 B2
(45) Date of Patent: Dec. 17, 2002

(54) BIOLOGICALLY ACTIVE ANALOGS OF DISCODERMOLIDE

(75) Inventors: Sarath P. Gunasekera, Vero Beach, FL (US); Ross E. Longley, Vero Beach, FL (US); Richard A. Isbrucker, Ontario (CA); Gopal K. Paul, Ft. Pierce, FL (US); Shirley A. Pomponi, Ft. Pierce, FL (US); Amy E. Wright, Ft. Pierce, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 09/796,175

(22) Filed: Feb. 28, 2001

(65) Prior Publication Data

US 2001/0049387 A1 Dec. 6, 2001

Related U.S. Application Data

(60) Provisional application No. 60/186,145, filed on Mar. 1, 2000.

(51) Int. Cl.$^7$ .................... A61K 31/35; A61K 31/215
(52) U.S. Cl. ............... 514/459; 514/460; 514/529; 549/292; 560/183
(58) Field of Search ................. 514/459, 460, 514/529; 549/292; 560/183

(56) References Cited

U.S. PATENT DOCUMENTS

| | | | |
|---|---|---|---|
| 4,206,221 A | 6/1980 | Miller et al. | 514/471 |
| 4,808,590 A | 2/1989 | Higa et al. | 514/272 |
| 4,939,168 A | 7/1990 | Gunaskera et al. | 514/559 |
| 4,960,790 A | 10/1990 | Stella et al. | 514/449 |
| 5,010,099 A | 4/1991 | Gunasekera et al. | 514/459 |
| 5,157,049 A | 10/1992 | Haugwitz et al. | 514/449 |
| 5,681,847 A | 10/1997 | Longley et al. | 514/459 |
| 5,789,605 A | 8/1998 | Smith, III et al. | 514/459 |
| 5,840,750 A | 11/1998 | Longley et al. | 514/459 |
| 6,127,406 A | 10/2000 | Gunasekera et al. | 514/459 |

FOREIGN PATENT DOCUMENTS

| | | |
|---|---|---|
| GB | 2280677 | 7/1994 |
| WO | 98/4429 | 12/1997 |
| WO | 98/24427 | 12/1997 |

OTHER PUBLICATIONS

Balachandran, R., ter Haar, E., Welsh, M.J., Grant, S.G., and Day, B.W. (1998) *Anticancer Drugs* 9: 67–76.
Faulkner, D.J. (1998) *Natural Products Reports* 15:113–158.
Fuchs, D.A., R.K. Johnson [1978] *Cancer Treat. Rep.* 62:1219–1222.
Gunasekera, S.P., M. Gunasekera, R.E. Longley and G.K. Schulte (1990) *J. Org. Chem.*, 55:4912–4915 [correction (1991) *J. Org. Chem.* 56:1346].
Harried, Scott H., Ge Yang, Marcus A. Strawn, David C. Myles (1997) *J. Org. Chem.* 62:6098–6099.
Hung, Deborah T., Jenne B. Nerenberg, Stuart Schreiber (1994) *Chemistry and Biology* 1:67–71.
Hung, Deborah T., Jie Cheng, Stuart Schreiber (1996) *Chemistry and Biology* 3:287–293.
Kowalski, R.J., P. Giannakakou, S.P. Gunasekera et al. (1997) *Mol. Pharmacol* 52:613–622.
Nerenberg, Jennie B., Deborah T. Hung, Patricia K. Somers, Stuart L. Schreiber (1993) *J. Amer. Chem. Soc.* 115:12621–12622.
Rowinski, E.K. R.C. Donehower [1995] *N. Engl. J. Med.* 332:1004–1014.
Schiff, P.B., J. Fant, S.B. Horwitz [1979] *Nature* (London) 22:665–667.
Smith III, Amos B., Yuping Qiu, David R. Jones, Karoru Kobayashi (1995) *J. Amer. Chem. Soc.* 117:12011–12012.
Stafford, J.A. and M. M. Mehrotra (1995) *Chemtract: Org. Chem.* 8:41–47.
ter Haar, E., R.J. Kowalski, E. Hamel et al. (1996) *Biochemistry* 35:243–250.

*Primary Examiner*—Amelia Owens
(74) *Attorney, Agent, or Firm*—Saliwanchik, Lloyd & Saliwanchik

(57) ABSTRACT

The subject invention provides novel compositions of biologically active discodermolide compounds which can advantageously be used for immunomodulation and/or treating cancer. The compounds of the subject invention have utility for use in the treatment of cancer, as tubulin polymerizers and as microtubule stabilization agents. The present invention also pertains to the identification of regions of the discodermolide molecule which are responsible for certain aspects of the bioactivity of discodermolide compounds.

31 Claims, 9 Drawing Sheets

Discodermolide (I)

2-Desmethyldiscodermolide (II)

19-Desaminocarbonyldiscodermolide (III)

2-Epidiscodermolide (IV)

Methyldiscodermolate (V)

3-Deoxy-2Δ-discodermolide (VI)

3-Deoxy-2Δ-discodermolide-17-acetate (VII)

3-Deoxy-2Δ-discodermolide-11,17-diacetate (VIII)

3-Deoxy-2Δ-discodermolide-7,11,17-triacetate (IX)

3-Deoxy-2Δ-discodermolide-11-acetate (X)

3-Deoxy-2Δ-discodermolide-7-succinate (XI)

8,21,23-Hexahydrodiscodermolide (XII)

7-Deoxy-8,21,23-hexahydrodiscodermolide (XIII)

7-Deoxy-8,21,23-hexahydrodiscodermolide-3,11,17-triacetate (XIV)

Control

Discodermolide (100 nM)

8,21,23-Hexahydro-discodermolide(100 nM)

7-Deoxy-8,21,23-hexahydrodiscodermolide (100nM)

7-Deoxy-8,21,23 hexahydrodiscodermolide
(1000 nM)

7-Deoxy-8,21,23-hexahydrodiscodermolide-
3,11,17-triacetate (1000 nM)

BIOLOGICALLY ACTIVE ANALOGS OF DISCODERMOLIDE

CROSS-REFERENCE TO A RELATED APPLICATION

This application claims priority from provisional application U.S. Ser. No. 60/186,145, filed Mar. 1, 2000.

The subject invention was made with government support under a research project supported by National Institutes of Health Grant No. ROI CA 74227. The government has certain rights in this invention.

FIELD OF THE INVENTION

This invention relates to organic compounds and compositions which have useful therapeutic properties. More particularly, the invention concerns novel discodermolide compounds having immunomodulatory and antitumor activities, pharmaceutical compositions comprising such compounds, and methods of their use for therapeutic purposes. Another aspect of the present invention pertains to the identification of regions of the discodermolide molecule which are responsible for certain aspects of the bioactivity of discodermolide.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed.

In searching for new biologically active compounds, it has been found that some natural products and organisms are potential sources for chemical molecules having useful biological activity of great diversity. For example, the diterpene commonly known as Taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature (London)* 22:665–667). Taxol is also known to have antitumor activity and has undergone a number of clinical trials which have shown it to be effective in the treatment of a wide range of cancers (Rowinski, E. K. R. C. Donehower [1995] *N. Engl. J Med.* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1998) *Natural Products Reports* 15:113–158; Gunasekera, S. P., M. Gunasekera, R. E. Longley and G. K. Schulte (1990) "Discodermolide: A new bioactive polyhydroxy lactone from the marine sponge *Discodermia dissoluta*" *J. Org. Chem.*, 55:4912–4915 [correction (1991) *J. Org. Chem.* 56:1346]; Hung, Deborah T., Jenne B. Nerenberg, Stuart Schreiber (1994) "Distinct binding and cellular properties of synthetic (+)- and (−)- discodermolides" *Chemistry and Biology* 1:67–71; Hung, Deborah T., Jie Cheng, Stuart Schreiber (1996) (+)-Discodermolide binds to microtubules in stoichiometric ratio to tubulin dimers, blocks Taxol binding and results in mitotic arrest" *Chemistry and Biology* 3:287–293; Nerenberg, Jennie B., Deborah T. Hung, Patricia K. Somers, Stuart L. Schreiber (1993) "Total synthesis of immunosuppressive agent (−)-discodermolide" *J. Amer. Chem. Soc.* 115:12621 –12622; Smith III, Amos B., Yuping Qiu, David R. Jones, Karoru Kobayashi (1995) "Total synthesis of (−) discodernolide" *J. Amer. Chem. Soc.* 117:12011–12012; Harried, Scott H., Ge Yang, Marcus A. Strawn, David C. Myles (1997) "Total synthesis of (−)-discodermolide: an application of a chelation-controlled alkylation reaction" *J. Org. Chem.* 62:6098–6099; Balachandran, R., ter Haar, E., Welsh, M. J., Grant, S. G., and Day, B. W. (1998) "The potent microtubule-stabilizing agent (+)-discodermolide induces apoptosis in human breast carcinoma cells-preliminary comparisons to paclitaxel." *Anticancer Drugs* 9: 67–76 and references cited therein. U.S. Pat. No. 4,808,590 discloses compounds, having antiviral, antitumor, and antifungal properties, isolated from the marine sponge Theonella sp. (International Patent Application No. WO 9824429; Kowalski, R. J., P. Giannakakou, S. P. Gunasekera et al. (1997) *Mol. Pharmacol* 52:613–622; ter Haar, E., R. J. Kowalski, E. Hamel et al. (1996) *Biochemistry* 35:243–250; Stafford, J. A. and M. M. Mehrotra (1995) *Chemtract: Org. Chem.* 8:41–47; and U.S. Pat. No. 5,789,605.

BRIEF SUMMARY OF THE INVENTION

A principal object of the subject invention is the provision of novel compositions of biologically active discodermolide analogs which can advantageously be used for immunomodulation and/or treating cancer. The compounds of the subject invention have utility for use in the treatment of cancer, and as tubulin polymerizers and as microtubule stabilization agents.

In a specific embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

The subject invention provides new analogs of discodermolide which, advantageously, possess useful biological activity against tumors and other forms of cancer. Another aspect of the present invention pertains to the identification of regions of the discodermolide molecule which are responsible for certain aspects of the bioactivity of discodermolide.

In specific embodiments, the subject invention provides four new analogs of discodermolide isolated from nature and nine new analogs of discodermolide produced through organic synthesis. The compounds of the subject invention have not been isolated previously from a natural source nor have they been previously synthesized. These compounds indicate the effects on biological activity caused by 1)

modification of functionality located at the lactone end of the molecule; 2) reduction of selected double bonds present in the molecule and 3) the contribution of the carbamate functionality towards the biological activity.

Included in these embodiments are analogs which can be prepared through modifications to five regions of the discodermolide molecule, those being 1) the C-1 through C-7 lactone and connector region, 2) the C-8 through C-15 first hairpin, 3) the C-16 through C-20 second hairpin, 4) the C-21 through C-24 diene and 5) the carbamate at C-19. The activity of the compounds vary according to the region(s) modified. The structure activity data promotes the C-8 through C-15 and C-16 through C-20 hairpin regions as critical to the activity of the discodermolide molecule by providing an optimal spatial relationship between the C-11 hydroxyl and the C-17 hydroxyl functionalities found in natural and synthetic analogs which are essential for induction of tubulin polymerization and stabilizing of the microtubule network, thus causing a block in the cell cycle at the $G_2/M$ checkpoint. In addition, the C-1 though C-7 lactone and connector region provide a hydrogen bond acceptor such as a carbonyl group and the C-21 through C-24 diene region serve to provide a hydrophobic group; both functionalities being positioned in the same spatial relationship to the C-11 and C-17 hydroxyl groups as is found in discodermolide and active analogs.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

Figure 1:
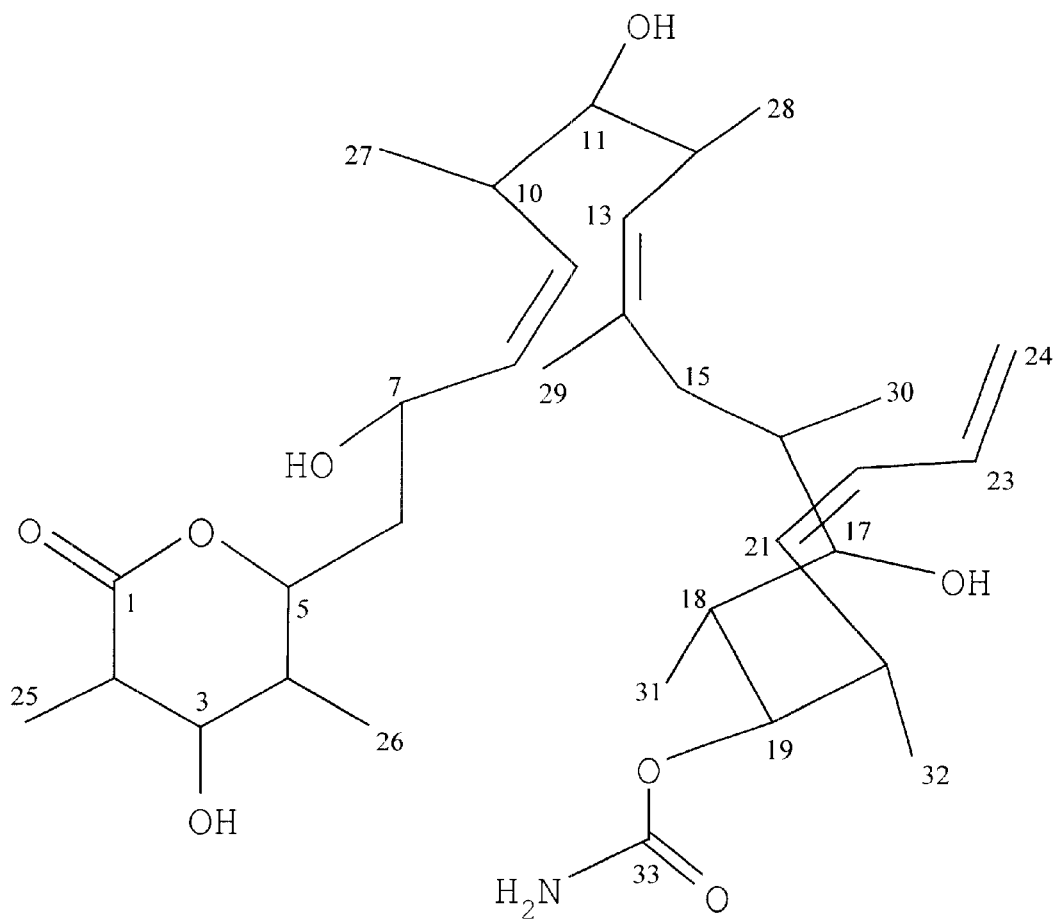
FIG. 1 shows the discodermolide molecule which can be divided into five general regions: the C-1 through C-7 lactone and connector region, the C-8 through C-15 first hairpin, the C-16 through C-20 second hairpin, the C-21 through C-24 diene and the carbamate at C-19. Activity of the discodermolide molecule varies according to the region (s) modified. The structure activity data identifies the C-8 through C-15 and C-16 through C-20 hairpin regions as critical to the activity of the discodermolide molecule by providing an optimal spatial relationship for the C-11 hydroxyl and the C-17 hydroxyl functionalities found in natural and synthetic analogs which are essential for induction of tubulin polymerization and stabilizing of the microtubule network, thus causing a block in the cell cycle at the $G_2/M$ checkpoint. In addition, the C-1 though C-7 lactone and connector region provide a hydrogen bond acceptor such as a carbonyl group and the C-21 through C-24 diene region serve to provide a hydrophobic group; both functionalities being positioned in the same spatial relationship to the C-1 and C-17 hydroxyl groups as is found in discodermolide and active analogs.
Figure 2:
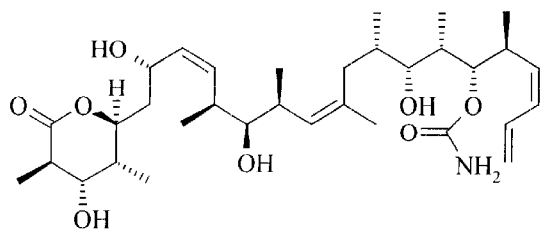
FIG. 2 shows the structures of discodermolide (I) and certain natural analogs of discodermolide (Compounds II–V) of the subject invention.
Figure 2:
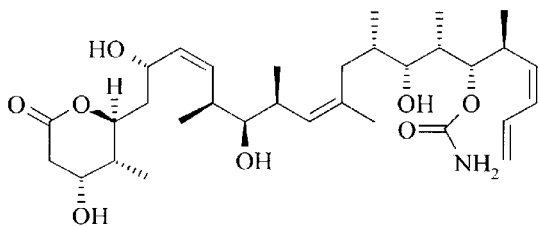
Figure 2:
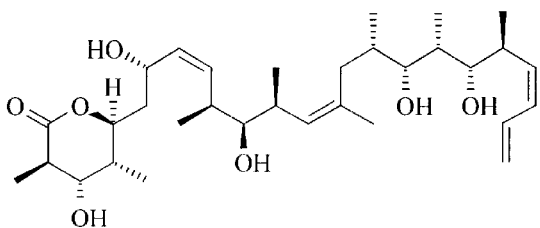
Figure 2:
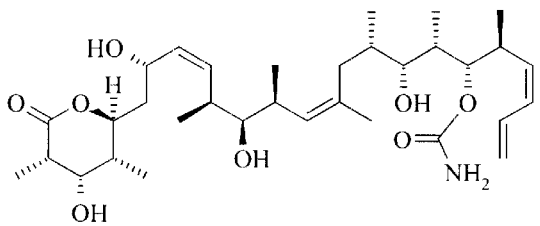
Figure 2:
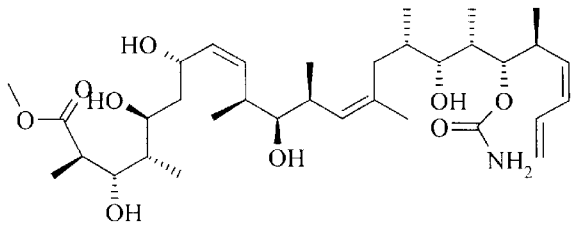
Figure 3A:
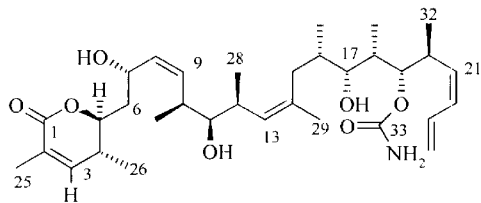
FIGS. 3A–B shows the structures of certain semi-synthetic analogs of discodermolide (Compounds VI–XIV) of the subject invention.
Figure 3A:
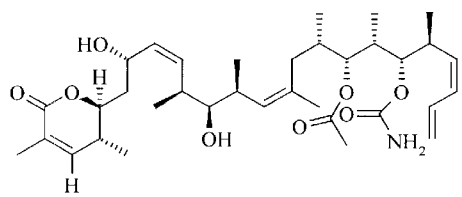
Figure 3A:
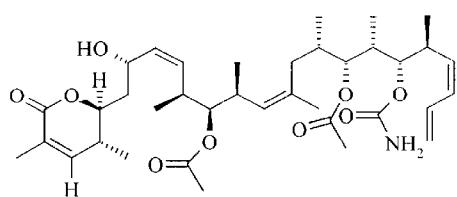
Figure 3A:
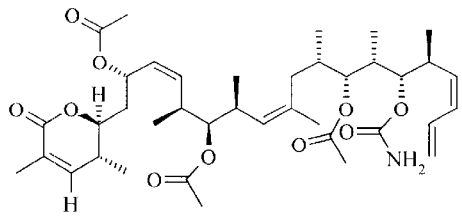
Figure 3A:
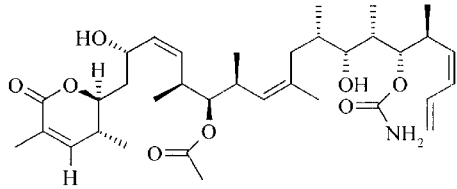
Figure 3A:
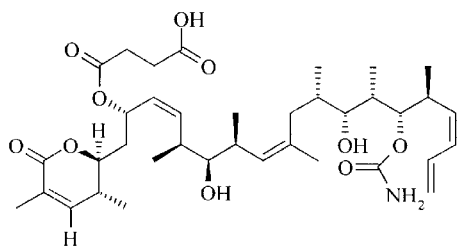
Figure 3B:
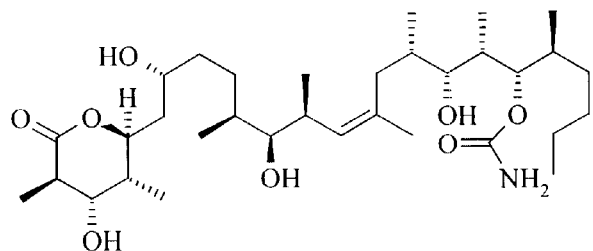
Figure 3B:
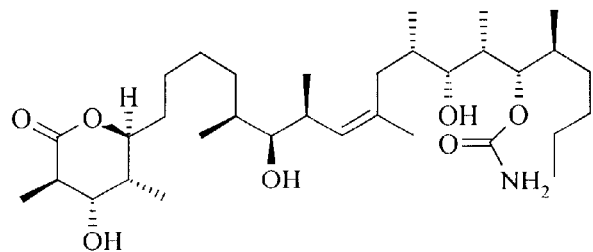
Figure 3B:
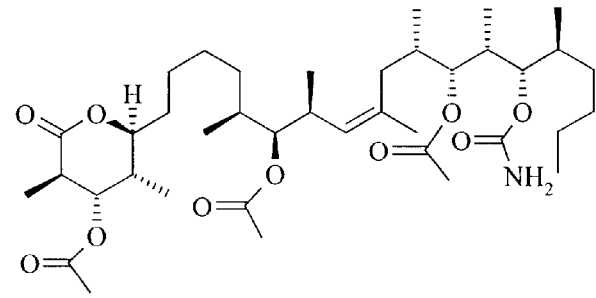

(6A)—shows untreated control cells;

(6B)—shows cells treated with 100 nM discodermolide (I);

(6C)—shows cells treated with 100 nM 8,21,23-hexahydrodiscodermolide (XII);

(6D)—shows cells treated with 100 nM 7-deoxy-8,21,23-hexahydrodiscodermolide (XIII);

(6E)—shows cells treated with 100 nM 7-deoxy-8,21,23-hexahydrodiscodermolide (XIII); and (6F)—shows cells treated with 1000 nM 7-deoxy-8,21, 23-hexahydrodiscodermolide-3,11,17-triacetate (XIV).

DETAILED DISCLOSURE OF THE INVENTION

The subject invention provides novel compositions of biologically active discodermolide compounds which are useful for immunomodulation and/or treating cancer. More specifically, the novel compounds, compositions and methods of use can advantageously be used to inhibit the growth of tumor and other cancer cells in a mammalian host. As described herein, the compounds of the subject invention have utility for use in the treatment of cancer, as tubulin polymerizers and as microtubule stabilizing agents. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells.

In accordance with the invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of improving immune responses and methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells. In addition to the types of cancer cells listed above for which the subject discodermolides and compositions are particularly useful, the subject compounds have also been shown to be useful for their antiproliferative activity against certain CNS cancer cell lines, melanoma cell lines, ovarian cancer cell lines, renal cancer cell lines, and prostate cancer cell lines. It would be expected, based on the particular antiproliferative modes of action identified herein, that additional cancer cell lines would also be inhibited by these compounds.

Various enantiomers of the discodermolides, as defined above, can be synthesized by persons of ordinary skill in the art. The natural discodermolide isolated from marine sponges is predominantly found to be the (+) enantiomer.

In preferred embodiments of the invention, the compounds are substantially pure, i.e., contain at least 95% of the compound as determined by established analytical methods.

Discodermolide compounds and methods of preparing those compounds or compositions comprising them, are described in U.S. Pat. Nos. 4,939,168; 5,010,099; 5,681, 847; and 5,840,750, and 6,127,406 which are hereby incorporated by reference.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

Analogs are compounds which are structurally related to discodermolide(I), including natural and synthetic derivatives, metabolites and intermediates.

In accordance with the subject invention it has been determined that analogs of discodermolide where the left side of the molecule is acetylated at positions C-3 and C-7, have greater cytotoxicity. This can be seen with, for example, discodermolide-3-acetate, discodermolide-7-acetate, and discodermolide-3,7-diacetate. See, U.S. Pat. No. 6,127,406. Analogs with acetyl groups at position C-11, for example, discodermolide-3,11-diacetate and discodermolide-3,7,11-triacetate, show a reduced cytotoxicity as compared to the parent molecule, whereas compounds which include an acetylation at position C-17 cause a dramatic reduction in the activity of the analogs, as seen for discodermolide-3,7,11,17-tetraacetate, discodermolide-3,7, 17-triacetate and discodermolide-3,17-diacetate. From these data it can be concluded that the C-11 and C-17 hydroxyl groups contribute to the overall cytotoxicity of the discodermolide molecule.

The discodermolide molecule can be divided into five general regions: the C-1 through C-7 lactone and connector region, the C-8 through C-15 first hairpin, the C-16 through C-20 second hairpin, the C-21 through C-24 diene and the carbamate at C-19 (see FIG. 1). Activity of the discodermolide molecule varies according to the region(s) modified. The structure activity data establishes the C-8 through C-15 and C-16 through C-20 hairpin regions as critical to the activity of the discodermolide molecule by providing an optimal spatial relationship for the C-11 hydroxyl and the C-17 hydroxyl functionalities found in natural and synthetic analogs which are essential for induction of tubulin polymerization and stabilizing of the microtubule network, thus causing a block in the cell cycle at the G2/M checkpoint. In addition, the C-i though C-7 lactone and connector region provide a hydrogen bond acceptor such as a carbonyl group and the C-21 through C-24 diene region serve to provide a hydrophobic group; both functionalities being positioned in the same spatial relationship to the C-11 and C-17 hydroxyl groups as is found in discodermolide and active analogs.

Materials and Methods

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Isolation and Structure Elucidation of 2-desmethyldiscodermolide (II)

The sponge specimen, 23-XI-98–3–002, identified as Discodermia sp. (HBOI CatNo. 003:00973) was collected by a manned submersible off Lucaya, Grand Bahama Island, Bahamas (Latitude: 26° 30.727' N Longitude: 78° 35.026' W), at a depth of 515 feet and was stored at −20° C. until extraction. The wet sponge (2000 g) was soaked in ethanol (EtOH) and the concentrated EtOH extract partitioned between ethyl acetate (EtOAc) and water ($H_2O$). The EtOAc-soluble fraction was chromatographed over silica gel using a step gradient of EtOAc-MeOH as eluent. Fractions were monitored by thin layer chromatography and $^1$H NMR spectra for the presence of discodermolide and discodermolide analogs. The TLC pattern and the $^1$H NMR spectrum of the fraction that eluted with 2–5% MeOH/EtOAc showed the presence of a discodermolide analog in addition to discodermolide. This fraction on further purification by HPLC ($SiO_2$, 5 μm, 250×10 mm) with 7% MeOH/$CH_2Cl_2$ as eluent gave 2-desmethyldiscodermolide as a white solid (yield: 0.5 mg, 0.00002% of wet weight).

2-Desmethyldiscodermolide: $[\alpha]^{21}D$ 10.2° (c 0.1, MeOH); IR (neat/NaCl) $v_{max}$ 3374, 1721, 1710, 1323, 1037 cm$^{-1}$; HRFABMS (glycerol) m/z 580.3853, Δ 0.4 mmu for $C_{32}H_{53}NO_8$ (M+H)$^+$. See Tables 1 and 2 for $^1$H and $^{13}$C NMR spectra, respectively.

The $^1$H NMR spectrum of 2-desmethyldiscodermolide was very similar to that of discodermolide with the primary difference being the presence of resonances for only seven methyl groups instead of the eight methyl groups observed for discodermolide. Detailed analysis of the $^1$H NMR indicated the absence of the C-2 methyl group signal which generally appears downfield due to deshielding by the adjacent carbonyl group. The DEPT spectrum showed the replacement of the C-2 methine carbon by a methylene carbon appearing at 40.3 ppm. The COSY spectrum clearly showed the coupling of these new methylene protons observed at 2.52 and 2.56 ppm to the C-3 hydroxy methine observed at 3.95 ppm. These data together with the mass spectral data confirmed the structure of 2-desmethyldiscodermolide.

EXAMPLE 2

Isolation and Structure Elucidation of 19-desaminocarbonyldiscodermolide (III)

The sponge specimen, 23-XI-98-3-001, identified as Discodermia sp. (HBOI Cat No. 003:00972) was collected by a manned submersible off Lucaya, Grand Bahama Island, Bahamas (Latitude: 26° 30.727' N Longitude: 78° 35.026' W), at a depth of 515 feet and was stored at −20° C. until extraction. The wet sponge (2480 g) was soaked in EtOH and the concentrated EtOH extract partitioned between EtOAc and H$_2$O. The EtOAc-soluble fraction was chromatographed over silica gel with MeOH/EtOAc. Fractions were monitored by thin layer chromatography and $^1$H NMR for the presence of discodermolide and discodermolide analogs. The $^1$H NMR spectrum of the fraction that eluted with 0–2% MeOH/EtOAc showed the presence of a discodermolide analog in addition to discodermolide. This fraction on further purification by HPLC (SiO$_2$, 5 μm, 250×10 mm) with 6% MeOH/CH$_2$Cl$_2$ as eluent followed by HPLC on the same column using 3% MeOH/CH$_2$Cl$_2$ as eluent gave 19-desaminocarbonyldiscodermolide as a white solid (yield: 1.1 mg, 0.00006% of wet weight).

19-Desaminocarbonyldiscodermolide: $[\alpha]^{21}D$ 18.0° (c 0.1, MeOH); IR (neat/NaCl) $v_{max}$ 3393, 1103,1030 cm$^{-1}$; HRFABMS (glycerol) m/z 551.3937, Δ 1.0 mmu for C$_{32}$H$_{54}$O$_7$ (M+H)$^+$. See Tables 1 and 2 for $^1$H and $^{13}$C NMR spectra, respectively.

The $^1$H NMR spectrum of 19-desaminocarbonyldiscodermolide was nearly identical to that of discodermolide. The $^1$H NMR spectrum indicated the absence of the characteristic two-proton signal for the aminocarbonyl group which appears as a broad signal at 5.05 ppm in discodermolide. The aminocarbonyloxy methine proton that appears at 4.71 ppm in discodermolide showed an upfield shift to 3.41 ppm indicating the presence of a typical hydroxy substituted methine proton instead of an aminocarbonyloxy methine proton at the C-19 position. The $^{13}$C NMR spectrum showed the absence of a signal corresponding to the aminocarbonyloxy carbon which appears at 158.4 ppm in discodermolide. These data together with the mass spectral data, confirmed the structure of 19-desaminocarbonyl- discodermolide.

EXAMPLE 3

Isolation and Structure Determination of 2-epidiscodermolide (IV)

The sponge specimen, 23-XI-98-1-005, identified as Discodermia sp. (HBOI Museum Catalog Number 003:00971) was collected by a manned submersible off the Bell Channel Buoy, Grand Bahama Island, Bahamas, (Latitude 26° 30.662'N, Longitude 78° 34.976' W) at a depth of 482 feet and was stored at −20° C. until extraction. The wet sponge (1931 g) was soaked in EtOH and the concentrated EtOH extract partitioned between EtOAc and H$_2$O. The EtOAc-soluble fraction was chromatographed over silica gel with CH$_2$Cl$_2$ followed by EtOAc-MeOH gradient. Fractions were monitored by thin layer chromatography and $^1$H NMR for discodermolide and discodermolide analogs. The fraction which eluted with 5% MeOH /EtOAc showed the presence of a discodermolide analog which on further purification by HPLC (SiO$_2$, 5 μm, 250×10 mm) using 6% MeOH/CH$_2$Cl$_2$ as eluent gave 2-epidiscodermolide as a white solid (yield 0.3 mg, 0.00001% of wet weight).

2-Epidiscodermolide: $[\alpha]^{21}D$ 10.7° (c 0.1, MeOH); IR(neat/NaCl) $v_{max}$ 3394,1720, 1041, 1028 cm$^{-1}$; HRFABMS (3-nitrobenzyl alcohol) m/z 594.4003, Δ 0.2 mmu for C$_{33}$H$_{55}$NO$_8$ (M+H)$^+$. See Tables 1 and 2 for $^1$H and $^{13}$C NMR spectra, respectively.

The $^1$H and $^{13}$C NMR spectra of 2-epidiscodermolide were very similar to that of discodermolide and indicated minor chemical shift and coupling constant differences around the lactone functionality. The NOESY spectrum of discodermolide shows correlations between the C-2-Me and C-3 -H, the C-2-H and C-3-H, the C-4-Me and C-3 -H, and the C-3-H and C-4-H all of which are in agreement with the reported structure in which there is an axial methyl at C-2, an axial hydroxyl at C-3 and an equatorial methyl at C-4. The NOESY spectrum of 2-epidiscodermolide showed correlations between the C-2-Me and C-3-H, the C-2-H and C-4-H, the C-4-Me and C-3-H, and the C-3-H and C-4-H. The strong NOE correlation between C-2-H and C-4-H indicated the one-three diaxial arrangement of these hydrogens. These data confirmed that the C-2-Me, which has an axial arrangement in discodermolide, has flipped to an equatorial arrangement in 2-epidiscodermolide. The above data together with the high resolution mass spectral data confirmed the structure of 2-epidiscodermolide.

TABLE 1

$^1$H NMR Data of Natural Analogs of Discodermolide
500 MHz, chemical shifts in ppm, referenced from solvent

| Position | 2-Desmethyl discodermolide (CD$_3$CN) δ$_H$ (mult. J in Hz) | 19-Desaminocarbonyl discodermolide (CD$_3$CN) δ$_H$ (mult. J in Hz) | 2-Epidiscodermolide (CD$_3$CN) δ$_H$ (mult. J in Hz) |
|---|---|---|---|
| 2 | 2.54 (dd, 3.2, 17.6) | 2.56 (dq, 6.2, 7.2) | 2.48 (dq, 2.5, 7.5) |
| 2 | 2.50 (d, 3.6, 17.6) | — | — |
| 3 | 3.95 (ddd, 3.2, 3.6, 5.8) | 3.63 (dd, 5.0, 6.2) | 3.73 (dd, 2.5, 2.0) |
| 4 | 1.70 (m) | 1.80 (ddq, 2.2, 5.0, 6.9) | 1.79 (ddq, 2.0, 6.2, 10.0) |
| 5 | 4.51 (dt, 1.8, 10.9) | 4.44 (dt, 2.2, 10.1) | 4.45 (dt, 7.5, 10.0) |
| 6 | 1.71 (m) | 1.69 (ddd, 8.7, 10.1, 13.1) | 1.72 (m) |
| 6 | 1.48 (ddd, 2.3, 10.9, 12.2) | 1.49 (ddd, 2.6, 10.1, 13.1) | 1.48 (ddd, 2.5, 10.0, 12.5) |
| 7 | 4.46 (m) | 4.47 (ddd, 8.3, 10.1, 13.1) | 4.44 (m) |
| 8 | 5.38 (ddd, 1.0, 8.4, 10-9) | 5.35 (ddd, 2.2, 10.1, 11.3) | 5.38 (ddd, 2.5, 10.0, 11.2) |
| 9 | 5.54 (dd, 10.4, 10.9) | 5.49 (dd, 10.1, 10.1) | 5.54 (dd, 10.0, 11.2) |
| 10 | 2.62 (ddq, 5.4, 6.8, 10.4) | 2.62 (ddq, 6.1, 6.9, 10.1) | 2.62 (m) |
| 11 | 3.06 (dd, 6.8, 7.2) | 3.09 (dd, 5.2, 6.1) | 3.05 (m) |
| 12 | 2.27 (ddq, 6.6, 7.2, 10.0) | 2.35 (ddq, 5.2, 6.6, 10.0) | 2.27 (ddq, 2.5, 7.5, 10.0) |
| 13 | 4.96 (d, 10.0) | 5.03 (d, 10.0) | 4.96 (d, 10.0) |
| 15 | 1.78 (dd, 9.5, 12.7) | 1.79 (dd, 10.1, 10.9) | 1.76 (m) |
| 15 | 1.61 (dd, 10.9, 12.7) | 1.73 (m) | 1.61 (dd, 8.7, 11.2) |

TABLE 1-continued

1H NMR Data of Natural Analogs of Discodermolide
500 MHz, chemical shifts in ppm, referenced from solvent

| Position | 2-Desmethyl discodermolide (CD$_3$CN) $\delta_H$ (mult. J in Hz) | 19-Desaminocarbonyl discodermolide (CD$_3$CN) $\delta_H$ (mult. J in Hz) | 2-Epidiscodermolide (CD$_3$CN) $\delta_H$ (mult. J in Hz) |
|---|---|---|---|
| 16 | 1.71 (m) | 1.74 (m) | 1.72 (m) |
| 17 | 3.13 (dd, 4.1, 6.9) | 3.27 (dd, 4.4, 4.8) | 3.13 (dd, 6.2, 7.5) |
| 18 | 1.72 (m) | 1.72 (m) | 1.75 (m) |
| 19 | 4.72 (dd, 4.5, 4.5) | 3.41 (ddd, 2.5, 3.7, 7.5) | 4.71 (dd, 5.0, 5.0) |
| 20 | 3.08 (ddq, 4.1, 6.8, 10.4) | 2.84 (ddq, 6.5, 7.5, 10.5) | 3.07 (m) |
| 21 | 5.42 (ddd, 10.9, 10.4, 11.4) | 5.40 (ddd, 10.5, 10.5, 13.1) | 5.42 (ddd, 10.0, 11.2, 12.5) |
| 22 | 6.07 (ddd, 1.0, 11.3, 11.4) | 6.06 (ddd, 1.0, 10.5, 11.0) | 6.07 (ddd, 1.3, 10.0, 11.2) |
| 23 | 6.67 (dddd, 1.3, 10.1, 11.3, 16.8) | 6.68 (dddd, 1.3, 10.5, 10.9, 17.0) | 6.66 (dddd, 1.3, 10.0, 11.2, 16.4) |
| 24 | 5.24 (dd, 1.7, 16.8) | 5.21 (dd, 2.2, 17.0) | 5.24 (dd, 1.3, 16.4) |
| 24 | 5.14 (d, 10.1) | 5.10 (d, 10.5) | 5.14 (d, 10.0) |
| 25 | — | 1.19 (d, 7.2) | 1.16 (d, 7.5) |
| 26 | 1.01 (d, 6.8) | 0.97 (d, 6.9) | 1.02 (d, 6.2) |
| 27 | 1.01 (d, 6.8) | 1.00 (d, 6.9) | 1.00 (d, 5.4) |
| 28 | 0.88 (d, 6.6) | 0.90 (d, 6.6) | 0.88 (d, 7.5) |
| 29 | 1.57 (s) | 1.61 (s) | 1.56 (s) |
| 30 | 0.73 (d, 6.3) | 0.76 (d, 6.4) | 0.73 (d, 6.2) |
| 31 | 0.80 (d, 6.9) | 0.88 (d, 6.9) | 0.79 (d, 6.5) |
| 32 | 0.95 (d, 6.8) | 0.93 (d, 7.0) | 0.95 (d, 6.6) |

TABLE 2

13C NMR Data of Natural Analogs of Discodermolide
125.7 MHz, chemical shifts (ppm) referenced
from solvent, (multiplicity)

| Position | 2-Desmethyl-discodermolide CD$_3$CN | 19-Desaminocarbonyl discodermolide CD$_3$CN | 2-Epidiscodermolide CD$_3$CN |
|---|---|---|---|
| 1 | 170.7(s) | 174.7(s) | 174.3(s) |
| 2 | 40.3(t) | 44.1(d) | 43.5(d) |
| 3 | 68.2(d) | 73.2(d) | 73.1(d) |
| 4 | 38.3(d) | 36.3(d) | 39.9(d) |
| 5 | 78.1(d) | 77.6(d) | 78.8(d) |
| 6 | 42.6(t) | 42.2(t) | 42.9(t) |
| 7 | 63.3(d) | 63.6(d) | 63.4(d) |
| 8 | 133.9(d) | 133.7(d) | 134.0(d) |
| 9 | 133.8(d) | 133.8(d) | 133.8(d) |
| 10 | 36.4(d) | 36.5(d) | 36.3(d) |
| 11 | 79.8(d) | 79.6(d) | 79.8(d) |
| 12 | 37.2(d) | 36.9(d) | 37.2(d) |
| 13 | 131.2(d) | 131.2(d) | 131.2(d) |
| 14 | 133.9(s) | 133.8(s) | 133.9(s) |
| 15 | 36.3(t) | 36.3(t) | 36.2(t) |
| 16 | 34.3(d) | 34.4(d) | 34.3(d) |
| 17 | 76.0(d) | 79.4(d) | 76.0(d) |
| 18 | 38.5(d) | 37.5(d) | 38.5(d) |
| 19 | 79.4(d) | 79.0(d) | 79.4(d) |
| 20 | 34.8(d) | 36.5(d) | 34.7(d) |
| 21 | 134.3(d) | 136.5(d) | 134.2(d) |
| 22 | 130.6(d) | 130.3(d) | 130.6(d) |
| 23 | 133.3(d) | 133.9(d) | 133.2(d) |
| 24 | 118.6(t) | 117.9(t) | 118.6(t) |
| 25 | — | 15.8(q) | 13.3(q) |
| 26 | 14.3(q) | 13.1(q) | 14.7(q) |
| 27 | 19.8(q) | 19.3(q) | 19.8(q) |
| 28 | 17.6(q) | 17.1(q) | 17.6(q) |
| 29 | 23.3(q) | 23.5(q) | 23.3(q) |
| 30 | 15.5(q) | 15.4(q) | 15.6(q) |
| 31 | 9.1(q) | 7.2(q) | 9.1(q) |
| 32 | 18.2(q) | 18.1(q) | 18.2(q) |
| 33 | 158.4(s) | — | 158.4(s) |

EXAMPLE 4

Isolation and Structure Determination of Methyldiscodermolate (V)

The sponge specimen Discodermia sp. (23-XI-98-1 -003, HBOM Catalog Number 003:00970) was collected on Nov. 23, 1998, by a manned submersible off Bell Channel Bouy, Grand Bahama Islands, Bahamas, (Lat. 26° 30.662' N; Long. 78° 34.976' W) at a depth of 493 feet and was stored at −20° C. until extraction. The wet sponge 3570 g was soaked in EtOH and the concentrated EtOH extract partitioned between EtOAc and H$_2$O. The EtOAc-soluble fraction was chromatographed over silica gel with MeOH/EtOAc gradient and fractions monitored by thin layer chromatography and 1H NMR spectra for discodermolide and discodermolide analogs. The 1H NMR spectrum of the fraction that eluted with 0–2% MeOH/EtOAc showed a presence of a discodermolide analog in addition to discodermolide. This fraction on further purification by HPLC (SiO$_2$, 5 μm, 250×10 mm) with 7% MeOH/CH$_2$Cl$_2$ followed by HPLC with 4% MeOH/CH$_2$Cl$_2$ gave methyldiscodermolate as a white solid 1.1 mg (yield, 0.00003% of wet weight). Methyldiscodermolate: [α]$^{21}$D 14.6° (c 0.1, MeOH); IR (neat/NaCl) ν$_{max}$ 3361, 1710, 1393, 1046 cm$^{-1}$; HRFABMS (glycerol) m/z 626.4252, Δ1.6 mmu for C$_{34}$H$_{59}$NO$_9$ (M+H)$^+$. See Table 3 for 1H and 13C NMR spectra.

The 1H NMR spectrum of methyldiscodermolate as expected was very similar to that of discodermolide. The 1H NMR spectrum showed an additional three-proton singlet for a methoxy group at 3.63 ppm. The C-5 lactone-proton which appears at 4.46 ppm in discodermolide has shifted upfield to 3.90 ppm indicating the presence of a hydroxy group in this position. The 13C NMR spectrum showed a 4.6 ppm upfield shift for C-5 and a signal at 52.2 ppm characteristic for a methoxy group. The INAPT spectrum showed three-bond relation of the methoxy protons to the ester carbonyl at 176.7 ppm. These data together with mass spectral data confirmed the structure of discodermolide methylester.

TABLE 3

1H and 13 C NMR Data of Methyldiscodermolate (V)
Chemical shifts in ppm, referenced from solvent

| Position | $\delta_H$ (mult. J in Hz) 500 MHz, (CD$_3$CN) | $\delta_C$ (mult. J in Hz) 125 MHz, (CD$_3$CN) |
|---|---|---|
| 1 | — | 176.7(s) |
| 2 | 2.66 (1H dq, 3.2, 7.0) | 43.1(d) |
| 3 | 3.91 (1H, dd 4.0, 3.2) | 76.6(d) |
| 4 | 1.64 (1H, ddq, 3.2, 7.1, 10.5) | 42.0(d) |
| 5 | 3.90 (1H, dt, 3.2, 10.5) | 73.0(d) |
| 6 | 1.45 (1H, ddd 3.2, 10.5, 13.9) | 41.7(t) |
| 6 | 1.63 (1H, ddd, 2.4, 6.8, 13.9) | — |
| 7 | 4.50 (1H, overlapping m) | 65.6(d) |
| 8 | 5.41 (1H, overlapping m) | 134.5(d) |
| 9 | 5.45 (1H, overlapping m) | 134.2(d) |
| 10 | 2.64 (1H, ddq, 7.0, 8.0, 7.6) | 36.5(d) |
| 11 | 3.07 (1H, dd 4.9, 8.0) | 79.7(d) |
| 12 | 2.36 (1H, ddq, 4.9, 6.6, 10.0) | 36.5(d) |
| 13 | 5.03 (1H, d, 10.0) | 131.2(d) |
| 14 | — | 133.8(s) |
| 15 | 1.68 (1H, dd, 12.1, 8.9) | 36.3 (t) |
| 15 | 1.79 (1H, dd, 12.1, 10.4) | — |
| 16 | 1.78 (1H, overlapping m) | 34.3(d) |
| 17 | 3.14 (1H, dd, 6.7, 8.8) | 76.1(d) |
| 18 | 1.80 (1H, overlapping m) | 38.4(d) |
| 19 | 4.70 (1H, dd, 4.5, 4.7) | 79.1(d) |
| 20 | 3.08 (1H, overlapping m) | 34.9(d) |
| 21 | 5.42 (1H, overlapping m) | 133.3(d) |

TABLE 3-continued

¹H and 13 C NMR Data of Methyldiscodermolate (V)
Chemical shifts in ppm, referenced from solvent

| Position | $\delta_H$ (mult. J in Hz) 500 MHz, (CD₃CN) | $\delta_C$ (mult. J in Hz) 125 MHz, (CD₃CN) |
|---|---|---|
| 22 | 6.04 (1H, dd, 11.0, 12.1) | 130.4(d) |
| 23 | 6.67 (1H, dddd, 1.0, 11.0, 8.8, 18.7) | 133.6(d) |
| 24 | 5.13 (1H, d, 11.0) | 118.3(t) |
| 24 | 5.23 (1H, dd, 1.6, 18.7) | — |
| 25 | 1.07 (3H, d, 7.0) | 9.3(q) |
| 26 | 0.76 (3H, d, 7.1) | 12.9(q) |
| 27 | 0.98 (3H, d, 7.0) | 19.3(q) |
| 28 | 0.88 (3H, d, 6.6) | 16.7(q) |
| 29 | 1.59 (3H, s) | 23.4(q) |
| 30 | 0.74 (3H, d, 6.3) | 15.2(q) |
| 31 | 0.84 (3H, d 6.6) | 9.2(q) |
| 32 | 0.95 (3H, d, 6.9) | 18.2(q) |
| 33 | — | 158.3(s) |
| 1-OCH₃ | 3.63 (3H, s) | 52.2(q) |

EXAMPLE 5

Preparation of 3-deoxy-2Δ-discodermolide (VI)

Discodermolide-3-acetate (2.4 mg), prepared as described in U.S. Pat. No. 6,127,406, was treated with 2 mL of saturated aqueous Na₂CO₃ in EtOH (1:9) and the mixture stirred for 24 hr. The solvent was concentrated by distillation under reduced pressure and the product was partitioned between EtOAc and H₂O. The EtOAc soluble fraction was concentrated and the residue after purification by HPLC (SiO₂, 5 μm, 250×10 mm) with 4.5% MeOH/CH₂Cl₂ as eluent gave 3-deoxy-2Δ-discodermolide as a white solid (1.2 mg, 50% yield).

The ¹H and ¹³C NMR spectra of 3-deoxy-2Δ-discodermolide (Tables 4 and 6, respectively) were similar to those observed for discodermolide. The ¹H NMR spectrum indicated signals for eight methyl groups. However, it showed the presence of two vinylic methyl singlets compared to one vinylic methyl in discodermolide. The comparison of the ¹H NMR spectrum of 3-deoxy-2Δ-discodermolide with that of discodermolide indicated that the downfield methyl doublet corresponding to the C-2-Me in discodermolide has been changed to a vinylic methyl group in 3-deoxy-2Δ-discodermolide. The ¹H—¹H COSY spectrum indicated coupling between the vinylic methyl at 1.88 ppm with the newly formed broad olefinic singlet observed at 6.33 ppm. Although, no coupling was seen between the olefinic singlet at 6.33 ppm and the C-4-H observed at 2.44 ppm, the allylic nature of the latter proton established the position of the new unsaturation. The remainder of the ¹H NMR spectrum was identical to that of discodermolide. The COSY spectral data were used to assign the chemical shift values for all protons in the compound. These data confirmed the structure of 3-deoxy-2Δ-discodermolide.

EXAMPLE 6

Preparation of 3-deoxy-2Δ-discodermolide-17-acetate (VII) and 3-deoxy-2Δ-discodermolide-11,17-diacetate (VIII)

Discodermolide-3,7,11,17-tetraacetate (4.0 mg), prepared as described in U.S. Pat. No. 6,127,406, was treated with 2 mL of saturated aqueous Na₂CO₃ in EtOH (1:9) and the mixture stirred at 40° C. for 4 hr. The solvent was concentrated under reduced pressure and the product was partitioned between EtOAc and H₂O. The EtOAc soluble fraction was concentrated and the residue after purification by HPLC (SiO₂, 5 μm, 250×10 mm, with 3.5% MeOH/CH₂Cl₂ as eluent) gave 3-deoxy-2Δ-discodermolide-17-acetate (1.0 mg) as a white solid and 3-deoxy-2Δ-discodermolide-11,17-diacetate as a white solid (2.0 mg).

The ¹H NMR spectrum of 3-deoxy-2Δ-discodermolide-17-acetate (Table 5) closely resembled that of 3-deoxy-2Δ-discodermolide (Table 4) and 3-deoxy-2Δ-discodermolide-11,17-diacetate (Table 4). However, the spectrum indicated the presence of one acetyl group at 2.07 ppm implying that three acetyl groups have undergone hydrolysis during the reaction. The presence of the vinylic methyl at 1.88 ppm together with the olefinic singlet at 6.32 indicated the presence of the 3-deoxy-2Δ functionality as in 3-deoxy-2Δ-discodermolide. The upfield shift of C-7-H (observed at 4.72 ppm) by 0.89 ppm and of C-11-H (observed at 3.12 ppm) by 1.49 ppm when compared to the C-7-H and C-11-H of discodermolide tetraacetate established the absence of acetyl groups at these positions. The remainder of the ¹H spectrum resembled that of discodermolide 3,7,11,17-tetraacetate. Careful analysis of the COSY spectrum assigned the chemical shift values for the remaining protons in the compound. ¹³C NMR data are reported in Table 6. These data confirmed the structure of 3-deoxy-2Δ-discodermolide-17-acetate.

The ¹H NMR spectrum of 3-deoxy-2Δ-discodermolide-11,17-diacetate (Table 4) closely resembled that of 3-deoxy-2Δ-discodermolide (Table 4). However, the spectrum indicated the presence of two acetyl groups observed at 2.08 and 2.04 ppm implying that two acetyl groups have undergone hydrolysis during the reaction. The presence of the vinylic methyl at 1.88 ppm together with the olefinic singlet at 6.32 indicated the presence of the 3-deoxy-2Δ functionality as in 3-deoxy-2Δ-discodermolide. The upfield shift of C-7-H (observed at 4.66 ppm) by 0.95 ppm when compared to the C-7-H of discodermolide tetraacetate (observed at 5.61 ppm) established the absence of an acetyl group at this position. The remainder of the ¹H spectrum resembled that of discodermolide 3,7,11,17-tetraacetate. Careful analysis of the COSY spectrum assigned the chemical shift values for the remaining protons in the compound. These data confirmed the structure of 3-deoxy-2Δ-discodermolide-11,17-diacetate.

TABLE 4

¹H NMR Data of Semi-synthetic
Analogs of Discodermolide (500 MHz), mult., J (Hz))

| Position | 3-Deoxy-2Δ-discodermolide (CD₃CN) | 3-Deoxy-2Δ-discodermolide-11,17-diacetate (CD₃CN) |
|---|---|---|
| 1 | — | — |
| 2 | — | — |
| 3 | 6.33 (1H, s) | 6.32 (1H, s) |
| 4 | 2.44 (dq, 9.5, 6.5) | 2.46 (m) |
| 5 | 4.32 (ddd, 2.5, 9.5, 9.5) | 4.30 (ddd, 2.2, 10.0, 10.0) |
| 6 | 1.80, 1.60 (2H, m) | 1.77, 1.67 (m) |
| 7 | 4.76 (ddd, 2, 8.1, 8.0) | 4.65 (m) |
| 8 | 5.49 (dd, 8.0, 10.5) | 5.39 (dd, 8.0, 10.5) |
| 9 | 5.40 (dd, 10.5, 10.5) | 5.49 (dd, 10.5, 10.5) |
| 10 | 2.79 (ddq, 6.1, 10.5, 6.9) | 2.86 (ddq, 10.5, 10.0, 6.9) |
| 11 | 3.17 (dd, 6.1, 6.1) | 4.65 (m) |
| 12 | 2.60 (ddq, 6.6, 9.9, 6.1) | 2.46 (m) |
| 13 | 5.16 (d, 9.7) | 4.94 (d, 10.0) |
| 14 | — | — |
| 15 | 1.90, 1.6 (m) | 1.90, 1.6 (m) |
| 16 | 1.90 (m) | 2.0 (m) |
| 17 | 3.26 (dd, 5.1, 5.3) | 4.77 (dd, 5.1, 5.3) |

TABLE 4-continued $^1$H NMR Data of Semi-synthetic
Analogs of Discodermolide (500 MHz), mult., J (Hz))

| Position | 3-Deoxy-2Δ-discodermolide (CD$_3$CN) | 3-Deoxy-2Δ-discodermolide-11,17-diacetate (CD$_3$CN) |
|---|---|---|
| 18 | 1.80 (ddq, 5.1, 5.8, 6.8) | 1.96 (m) |
| 19 | 4.70 (dd, 6.5, 5.8) | 4.59 (dd, 6.0, 6.0) |
| 20 | 2.97 (ddq, 6.5, 7.0, 10.5) | 3.15 (ddq, 6.0, 7.0, 10.5) |
| 21 | 5.34 (dd, 10.5, 10.9) | 5.33 (dd, 10.5, 10.9) |
| 22 | 6.01 (dd, 10.9, 10.9) | 6.04 (dd, 10.9, 11.0) |
| 23 | 6.58 (ddd, 10.2, 10.9, 16.3) | 6.74 (ddd, 10.2, 11.0, 16.5) |
| 24 | 5.10 (d, 10.2) | 5.16 (d, 10.2) |
| 24 | 5.18 (d, 16.3) | 5.22 (d, 16.5) |
| 25 | 1.88 (s) | 1.84 (s) |
| 26 | 1.08 (d, 6.5) | 1.09 (d, 7.2) |
| 27 | 1.00 (d, 6.9) | 0.94 (d, 6.9) |
| 28 | 0.93 (d, 6.6) | 0.83 (d, 6.7) |
| 29 | 1.64 (s) | 1.61 (s) |
| 30 | 0.82 (d, 6.2) | 0.67 (6.5) |
| 31 | 0.96 (d, 6.8) | 0.89 (d, 7.0) |
| 32 | 0.98 (d, 7.0) | 0.94 (d, 7.0) |
| 35 | — | 2.04 (s) |
| 37 | — | 2.08 (s) |
| NH$_2$ | 4.59 (br s) | 4.59 (br s) |

EXAMPLE 7

Preparation of 3-deoxy-2Δ-discodermolide-7,11,17-triacetate (IX)

3-Deoxy-2Δ-discodermolide-11,17-diacetate (1.0 mg) was dissolved in dry pyridine (0.5 mL) and treated with 20 mL of acetic anhydride. The mixture was stirred at room temperature for 4 hours. Distillation of the solvent under reduced pressure gave 3-deoxy-2Δ-discodermolide-7,11,17-triacetate as a white solid (1.0 mg, % yield 100%). The $^1$H NMR spectrum of 3-deoxy-2Δ-discodermolide-7,11,17-triacetate (Table 5) closely resembled that of 3-deoxy-2Δ-discodermolide-11,17-diacetate (Table 4). The $^1$H spectrum indicated the presence of three acetyl groups observed at 2.08, 2.01 and 1.99 ppm indicating the acetylation of the C-7-OH group in 3-deoxy-2Δ-discodermolide-11,17-diacetate. The presence of the vinylic methyl at 1.88 ppm together with the olefinic singlet at 6.30 ppm indicated the presence of the 3-deoxy-2Δ functionality as in 3-deoxy-2Δ-discodermolide-11,17-diacetate. The downfield shift of C-7-H to 5.64 ppm from 4.66 ppm in the starting compound, indicated the acetylation of the C-7-OH group. The remaining signals in the $^1$H spectrum resembled that of 3-deoxy-2Δ-discodermolide-11,17-diacetate. The chemical shift values for the remaining protons were assigned by analysis of the COSY spectrum of the compound. $^{13}$C NMR data are reported in Table 6. These data confirmed the structure of 3-deoxy-2Δ-discodermolide-7,11,17-triacetate.

EXAMPLE 8

Preparation of 3-deoxy-2Δ-discodermolide-11-acetate (X)

Discodermolide-3,7,11,-triacetate (3.0 mg) was treated with 2 mL of saturated aqueous Na$_2$CO$_3$ in EtOH (1:9) and the mixture was stirred at 25° C. for 24 hours. The solvent was removed by distillation under reduced pressure and the residue was partitioned between CH$_2$Cl$_2$ and H$_2$O. The CH$_2$Cl$_2$ soluble fraction was concentrated and the residue on cation by HPLC (SiO$_2$, 5 μm, 250×10 mm) using 2.5% MeOH/CH$_2$Cl$_2$ as eluent gave 3-deoxy-2D-discodermolide-11-acetate as a white solid as the major product (1.5 mg).

The $^1$H NMR spectrum of 3-deoxy-2Δ-discodermolide-11-acetate (Table 5) closely resembled that of 3-deoxy-2Δ-discodermolide (Table 4). The $^1$H spectrum indicated the presence of one acetyl group observed at 2.08 ppm indicating a monoacetylated product. Comparison of the $^1$H NMR spectrum of this compound with that of 3-deoxy-2Δ-discodermolide indicated the presence of an acetate at C-1. The C-11-H acetoxymethine proton appeared at 4.72 ppm indicating a downfield shift of 1.55 ppm compared to that observed for C-11-H in 3-deoxy-2Δ-discodermolide. The remaining signals in the $^1$H spectrum resembled that of 3-deoxy-2Δ-discoderrnolide. Analysis of the COSY spectrum assigned the chemical shift values for all protons in the compound. $^{13}$C NMR data are reported in Table 6. These data confirmed the structure of 3-deoxy-2Δ-discodermolide-11-acetate.

TABLE 5

$^1$H NMR Data of Semi-synthetic Analogs of
Discodermolide (500 MHz), mult., J (Hz)

| Position | 3-Deoxy-2Δ-discodermolide-17-acetate (CD$_3$CN) | 3-Deoxy-2Δ-discodermolide-7,11,17-triacetate (CD$_3$CN) | 3-Deoxy-2Δ-discodermolide-11-acetate (CD$_3$CN) |
|---|---|---|---|
| 1 | — | — | — |
| 2 | — | — | — |
| 3 | 6.32 (s) | 6.30 (s) | 6.33 (s) |
| 4 | 2.43 (m) | 2.42 (m) | 2.44 (dq, 9.8, 7.1) |
| 5 | 4.32 (ddd, 2.2, 10.0, 10.0) | 4.04 (ddd, 2.2, 10.0, 10.0) | 4.32 (ddd, 2.2, 9.8, 9.8) |
| 6 | 1.80, 1.60 (m) | 1.90, 1.75 (m) | 1.7, 1.8 (m) |
| 7 | 4.72 (ddd, 2.0, 8.0, 8.0) | 5.63 (ddd, 2.0, 8.2, 9.0) | 4.75 (dd, 8.0, 9.0) |
| 8 | 5.47 (dd, 8.0, 10.5) | 5.28 (dd, 9.0, 10.5) | 5.38 (dd, 10.5, 9.0) |
| 9 | 5.41 (dd, 10.5, 10.1) | 5.48 (dd, 10.5, 10.5) | 5.44 (dd, 10.5, 10.5) |
| 10 | 2.73 (ddq, 10.1, 10.1, 6.9) | 2.84 (ddq, 10.5, 6.1, 6.6) | 2.88 (ddq, 6.1, 10.5, 6.7) |
| 11 | 3.12 (m) | 4.65 (dd, 6.1, 6.1) | 4.73 (m) |
| 12 | 2.43 (m) | 2.51 (ddq, 6.8, 10.0, 6.1) | 2.62 (ddq, 6.1, 6.7, 9.7) |
| 13 | 5.12 (d, 10.5) | 4.95 (d, 10.0) | 4.94 (d, 9.7) |
| 14 | — | — | — |
| 15 | 1.9, 1.6 (m) | 1.8, 1.6 (m) | 1.6, 1.9 (m) |
| 16 | 2.05 (m) | 2.0 (m) | 1.9 (m) |
| 17 | 4.79 (dd, 5.7, 5.7) | 4.78 (dd, 5.8, 5.8) | 3.25 (dd, 4.9, 5.1) |
| 18 | 2.0 (m) | 1.95 (ddq, 5.8, 6.7, 6.0) | 1.85 (m) |
| 19 | 4.62 (dd, 6.2, 6.2) | 4.60 (dd, 6.0, 6.0) | 4.71 (m) |
| 20 | 3.12 (m) | 3.14 (ddq, 10.6, 60, 6.6) | 3.00 (ddq, 6.2, 10.8, 6.7) |
| 21 | 5.33 (dd, 10.5, 10.0) | 5.33 (dd, 10.6, 10.8) | 5.34 (dd, 10.8, 10.9) |
| 22 | 6.03 (dd, 11.0, 10.0) | 6.03 (dd, 10.8, 11.0) | 6.01 (dd, 10.9, 10.9) |
| 23 | 6.70 (ddd, 10.2, 11.0, 16.3) | 6.72 (ddd, 10.1, 11.0, 16.5) | 6.60 (ddd, 10.9, 10.2, 16.3) |
| 24 | 5.14 (d, 10.2) | 5.15 (d, 10.1) | 5.11 (d, 10.2) |
| 24 | 5.21 (d, 16.3) | 5.21 (d, 16.5) | 5.20 (d, 16.3) |
| 25 | 1.88 (s) | 1.88 (s) | 1.88 (s) |
| 26 | 1.09 (d, 7.3) | 1.10 (d, 7.0) | 1.09 (d, 7.1) |
| 27 | 0.98 (d, 6.7) | 0.96 (d, 6.6) | 0.98 (d, 6.7) |
| 28 | 0.90 (d, 6.6) | 0.87 (d, 6.8) | 0.87 (d, 6.7) |
| 29 | 1.62 (s) | 1.60 (s) | 1.61 (s) |
| 30 | 0.71 (d, 7.5) | 0.68 (6.7) | 0.80 (d, 5.8) |
| 31 | 0.91 (d, 6.9) | 0.90 (d, 6.7) | 0.98 (d, 6.7) |
| 32 | 0.96 (d, 7.0) | 0.96 (d, 6.6) | 0.98 (d, 6.7) |
| 35 | 2.07 (s) | 2.01 (s) | — |
| 37 | — | 2.08 (s) | — |
| 39 | — | 1.99 (s) | — |
| NH$_2$ | 4.51 | 4.53 | — |

TABLE 6

$^{13}C$ NMR Data of Semi-synthetic Analogs of Discodermolide, [125.7 MHz, chemical shifts reported in ppm referenced from the solvent peak (multiplicity)]

| Position | 3-Deoxy-2Δ-discodermolide (CD$_3$CN) | 3-Deoxy-2Δ-discodermolide-17-acetate (CDCl$_3$) | 3-Deoxy-2Δ-discodermolide-7,11,17-triacetate (CDCl$_3$) | 3-Deoxy-2Δ-discodermolide-11-acetate (CDCl$_3$) |
|---|---|---|---|---|
| 1 | 166.2 (s) | 164.7(s) | 165.4(s) | 165.5(s) |
| 2 | 127.5 (s) | 127.5(s) | 127.3(s) | 127.3(s) |
| 3 | 147.0 (d) | 144.8(d) | 145.5(d) | 145.6(d) |
| 4 | 34.8 (d) | 33.6(d) | 30.6(d) | 34.0(d) |
| 5 | 80.7 (d) | 79.4(d) | 79.9(d) | 79.9(d) |
| 6 | 35.9 (t) | 38.4 (t) | 40.5 (t) | 40.5 (t) |
| 7 | 63.1 (d) | 66.8(d) | 63.4(d) | 63.4(d) |
| 8 | 134.2 (d) | 128.0(d) | 132.3(d) | 132.2(d) |
| 9 | 134.0 (d) | 135.2(d) | 133.7(d) | 133.9(d) |
| 10 | 36.2 (d) | 35.0(d) | 34.5(d) | 35.0(d) |
| 11 | 79.8 (d) | 80.1(d) | 80.3(d) | 80.3(d) |
| 12 | 37.19d) | 33.9(d) | 33.9(d) | 34.3(d) |
| 13 | 131.1 (d) | 129.0(d) | 128.9(d) | 128.8(d) |
| 14 | 133.2 (s) | 133.2(s) | 133.5(s) | 133.9(s) |
| 15 | 41.8 (t) | 35.5 (t) | 35.4 (t) | 36.0 (t) |
| 16 | 34.3 (d) | 31.9(d) | 31.9(d) | 32.8(d) |
| 17 | 75.9 d | 77.9(d) | 77.9(d) | 75.6(d) |
| 18 | 38.5 (d) | 36.4(d) | 36.5(d) | 37.4(d) |
| 19 | 79.4 (d) | 78.0(d) | 78.1(d) | 78.5(d) |
| 20 | 34.6 (d) | 34.0(d) | 34.0(d) | 34.7(d) |
| 21 | 134.0 (d) | 132.9(d) | 132.9(d) | 133.7(d) |
| 22 | 130.5 (d) | 130.2(d) | 130.3(d) | 129.9(d) |
| 23 | 133.6 (d) | 132.2(d) | 132.3(d) | 132.3(d) |
| 24 | 118.2 (t) | 118.2 (t) | 118.2 (t) | 117.8 (t) |
| 25 | 16.9 (q) | 16.7(q) | 16.8(q) | 16.6(q) |
| 26 | 16.8 (q) | 16.3(q) | 16.6(q) | 16.2(q) |
| 27 | 19.7 (q) | 17.4(q) | 17.5(q) | 17.4(q) |
| 28 | 17.5 (q) | 16.7(q) | 16.8(q) | 16.8(q) |
| 29 | 23.2 (q) | 22.9(q) | 22.9(q) | 23.0(q) |
| 30 | 15.6 (q) | 13.7(q) | 13.9(q) | 13.8(q) |
| 31 | 8.9 (q) | 9.4(q) | 9.4(q) | 8.9(q) |
| 32 | 18.1 (q) | 17.4(q) | 18.7(q) | 18.6(q) |
| 33 | 158.3 (s) | 156.7(s) | 156.7(s) | 156.9(s) |
| 34 | — | 170.9 (s) | 170.9 (s) | — |
| 35 | — | 20.9(q) | 21.0(q) | — |
| 36 | — | 170.5 (s) | 170.7 (s) | 170.8(s) |
| 37 | — | 20.9(q) | 20.9(q) | 21.0(q) |
| 38 | — | 169.8(s) | — | — |
| 39 | — | 21.2(q) | — | — |

EXAMPLE 9

Preparation of 3-deoxy-2Δ-discodermolide-7-succinate (XI)

Discodermolide (10 mg) was dissolved in 4 mL of dry pyridine and treated with 2 mg of succinic anhydride. The mixture was stirred at room temperature for one week and then at 40° C. for another one week. The solvent was evaporated under a steam of nitrogen to give a white solid (~10 mg). The mixture was separated by HPLC using a SiO$_2$ semi-prep column (Phenomenex Luna column, 5μ, 250×10 mm) with 7% MeOH in CH$_2$Cl$_2$ as eluent to give three fractions: a non polar mixture; 2-epidiscodermolide (~1 mg); and unreacted discodermolide (5 mg). The non polar mixture was re-chromatographed by HPLC using a SiO$_2$ semi-prep column (Phenomenex Luna column, 5μ, 250×10 mm) with 5% MeOH in CH$_2$Cl$_2$ as eluent to give three fractions: a second non polar mixture, 3-deoxy-2Δ-discodermolide (2 mg) and 3-deoxy-2Δ-discodermolide-7-succinate (1 mg).

Comparison of the $^1$H and $^{13}$C NMR data of 3-deoxy-2Δ-discodermolide-7-succinate (Table 7) with those of 3-deoxy-2Δ-discodermolide (Table 4) revealed close similarities and indicated the possible dehydration of the C-3 hydroxyl group during the reaction. Absence of the C-25 methyl doublet as well as the C-3-H hydroxymethine proton along with observation of a new olefinic methyl group (δ 1.80, 3H, s) and an olefinic proton (δ 6.40, 1H, s) in the spectra of this compound confirmed this assumption. Presence of two additional carbonyl groups (δ 173.8, s; 172.3, s) and two additional methylene groups (δ 2.51, 4H, m; $^{13}$C δ 30.0, t; 29.2, t) suggested the formation of the succinate. The down field shift of the 7-hydroxymethine proton observed at 5.68 ppm compared to 4.76 ppm in 3-deoxy-2Δ-discodermolide confirmed the structure as 3-deoxy-2Δ-discodermolide-7-succinate.

TABLE 7

$^1$H and $^{13}$C Chemical Shifts of 3-Deoxy-2Δ-discodermolide-7-succinate (XI)

| Position | $^1$H NMR Data CD$_3$CN 500 MHz, δ (mult, J in Hz) | $^{13}$C NMR Data CD$_3$CN 125 MHz, δ (mult) |
|---|---|---|
| 1 | — | 165.8 (s) |
| 2 | — | 127.6 (s) |
| 3 | 6.40 (1H, s) | 146.7 (d) |
| 4 | 2.41 (1H, m) | 34.6 (d) |
| 5 | 4.03 (1H, ddd, 10.6, 9.2, 1.5) | 80.1 (d) |
| 6 | 2.04, 1.72 (2H, overlapping m) | 39.3 (t) |
| 7 | 5.68 (1H, t, 9.2) | 67.2 (d) |
| 8 | 5.35 (1H, dd, 10.6, 9.2) | 128.6 (d) |
| 9 | 5.62, (1H, t, 10.6) | 136.5 (d) |
| 10 | 2.65 (1H, overlapping m) | 36.7 (d) |
| 11 | 3.09 (1H, m) | 79.7 (d) |
| 12 | 2.26 (1H, m) | 36.9 (d) |
| 13 | 5.00 (1H, d, 9.9) | 131.1 (d) |
| 14 | — | 134.1 (s) |
| 15 | 1.81, 1.73 (2H, overlapping m) | 36.0 (t) |
| 16 | 1.72 (1H, overlapping m) | 34.2 (d) |
| 17 | 3.14 (1H, dd, 3.2, 3.0) | 76.0 (d) |
| 18 | 1.71 (1H, overlapping m) | 38.5 (d) |
| 19 | 4.72 (1H, dd, 4.0, 3.1) | 79.3 (d) |
| 20 | 2.65 (1H, overlapping m) | 34.7 (d) |
| 21 | 5.41 (1H, t, 10.5) | 134.2 (d) |
| 22 | 6.06 (1H, t, 10.5) | 130.5 (d) |
| 23 | 2.51 (1H, ddd, 16.8, 10.5, 10.2) | 133.2 (d) |
| 24 | 5.24 (1H, d, 16.8) | 118.0 (t) |
| 24 | 5.14 (1H, d, 10.2) | — |
| 25 | 1.80 (3H, s) | 16.9 (q) |
| 26 | 1.07 (3H, d, 7.3) | 16.6 (q) |
| 27 | 0.96 (3H, d, 6.5) | 19.0 (q) |
| 28 | 0.89 (3H, d, 6.5) | 17.4 (q) |
| 29 | 1.61 (3H, s) | 23.2 (q) |
| 30 | 0.77 (3H, d, 6.5) | 15.5 (q) |
| 31 | 0.74 (3H, d, 6.53) | 9.0 (q) |
| 32 | 0.95 (3H, d, 6.5) | 18.1 (q) |
| 33 | — | 158.3 (s) |
| NH$_2$ | 4.70 (2H, br s) | — |
| Succinyl | 2.51 (4H, overlapping m) | 30.0(s),29.2(s) |

EXAMPLE 10

Preparation of 8,21,23-hexahydrodiscodermolide (XII) and 7-deoxy-8,21,23-hexahydrodiscodermolide (XIII)

Discodermolide (34.0 mg) dissolved in EtOH (20 mL) was hydrogenated with H$_2$ in the presence of PtO$_2$ catalyst for 0.5 hour under balloon pressure. The catalyst was removed by filtration and the resulting solution concentrated under a stream of N$_2$ to give a mixture of hydrogenated products. The mixture was separated by HPLC using a SiO$_2$ semi-prep column (Phenomenex, 5μ, 250×10 mm) with 7% MeOH in CH$_2$Cl$_2$ as eluent to give 8,21,23-hexahydrodiscodermolide (9.0 mg); [α]²¹D −29.20° (c 1.2, MeOH) and 7-deoxy-8,21,23-hexahydrodiscodermolide (2.3 mg); [α]²¹D −19.8° (c 0.3, MeOH). Tables 8 and 9 below, show the ¹H and ¹³C NMR data for these two analogs, respectively.

TABLE 8

¹H and ¹³C NMR Data of 8,21,23-hexahydrodiscodermolide (XII)

| Position | ¹H NMR Data CD₃CN, 500 MHz, δ (mult., J in Hz) | ¹³C NMR Data CD₃CN, 125 MHz, δ (mult.) |
|---|---|---|
| 1 | — | 174.9 (s) |
| 2 | 2.36 (1H, overlapping m) | 44.1 (d) |
| 3 | 3.43 (1H, dd, 4.4, 4.1) | 73.2 (d) |
| 4 | 1.66, 2.44 (1H, overlapping m) | 37.0 (d) |
| 5 | 4.27 (dt, 9.2, 4.2) | 78.3 (d) |
| 6 | 1.39, 1.65 (2H, overlapping m) | 31.8 (t) |
| 7 | 3.50 (1H, m) | 68.1 (d) |
| 8 | 1.30, 1.03 (2H, overlapping m) | 35.8 (t) |
| 9 | 1.27 (2H, overlapping m) | 41.9 (t) |
| 10 | 1.27 (1H, overlapping m) | 29.9 (d) |
| 11 | 2.82 (1H, dd, 5.4, 5.4) | 80.8 (d) |
| 12 | 2.33 (1H, overlapping m) | 36.2 (d) |
| 13 | 4.84 (1H, d, 9.8) | 131.6 (d) |
| 14 | — | 133.6 (s) |
| 15 | 1.88, 1.72 (2H, overlapping m) | 37.3 (t) |
| 16 | 1.66 (1H, overlapping m) | 33.8 (d) |
| 17 | 2.97 (1H, dd, 5.2, 5.2) | 77.0 (d) |
| 18 | 1.66 (1H, overlapping m) | 38.0 (d) |
| 19 | 4.33 (1H, dd, 4.2, 4.5) | 79.6 (d) |
| 20 | 1.53 (1H, overlapping m) | 36.9 (d) |
| 21 | 0.83 (2H, m) | 27.3 (t) |
| 22 | 1.2 (2H, overlapping m) | 23.6 (t) |
| 23 | 1.1 (2H, overlapping m) | 37.0 (t) |
| 24 | 0.71 (3H, t 6.6) | 9.7 (q) |
| 25 | 1.00 (3H, d, 7.4) | 15.7 (q) |
| 26 | 0.76 (3H, d, 7.1) | 13.1 (q) |
| 27 | 0.67 (3H, (d, 6.9) | 17.6 (q) |
| 28 | 0.71 (3H, d, 6.6) | 16.9 (q) |
| 29 | 1.42 (3H, s) | 23.6 (q) |
| 30 | 0.56 (3H, d, 6.5) | 13.6 (q) |
| 31 | 0.69 (3H, d, 6.8) | 14.3 (q) |
| 32 | 0.65 (3H, d, 7.0) | 16.4 (q) |
| 33 | — | 158.5 (s) |
| NH₂ | 4.88 (2H, br s) | — |

TABLE 9

¹H and ¹³C Chemical Shifts Table of 7-Deoxy-8,21,23-hexahydrodiscodermolide (XIII)

| Position | ¹H NMR Data CDCl₃, 500 MHz δ (mult., J in Hz) | ¹³C NMR Data CDCl₃, 125 MHz, δ (mult.) |
|---|---|---|
| 1 | — | 174.2 (s) |
| 2 | 2.64 (1H, dq, 3.7, 7.4) | 43.2 (d) |
| 3 | 3.71 (1H, dd, 3.7, 3.7) | 73.4 (d) |
| 4 | 1.91 (1H, overlapping m) | 34.9 (d) |
| 5 | 4.30 (1H, ddd, 2.8, 8.2, 8.2) | 80.2 (d) |
| 6 | 1.55, 1.70 (2H, overlapping m) | 33.1 (t) |
| 7 | 1.39, 1.47 (2H, overlapping m) | 24.9 (t) |
| 8 | 1.49 (2H, overlapping m) | 30.3 (t) |
| 9 | 1.36, 1.38 (2H, overlapping m) | 29.2 (t) |
| 10 | 1.53 (1H, overlapping m) | 35.7 (d) |
| 11 | 3.13 (1H, dd, 5.5, 5.7) | 80.8 (d) |
| 12 | 2.57 (1H, ddq, 4.7, 3.4, 10.0) | 35.5 (d) |
| 13 | 5.03 (1H, d, 9.8) | 130.0 (d) |
| 14 | — | 133.2 (s) |
| 15 | 1.87, 2.11 (2H, overlapping m) | 36.5 (t) |
| 16 | 1.97 (1H, overlapping m) | 33.2 (d) |
| 17 | 3.29 (1H, dd, 5.3, 5.4) | 77.2 (d) |
| 18 | 1.93 (1H, overlapping m) | 37.1 (d) |
| 19 | 4.58 (1H, dd, 2.8, 7.7) | 80.2 (d) |
| 20 | 1.72 (1H, overlapping m) | 35.5 (d) |
| 21 | 1.08, 1.16 (2H, overlapping m) | 31.4 (t) |
| 22 | 1.48 (2H, overlapping m) | 27.2 (t) |
| 23 | 1.25, 1.34 (2H, overlapping m) | 22.9 (t) |
| 24 | 0.86 (3H, t, 6.6) | 14.1 (q) |
| 25 | 1.29 (3H, d, 7.3) | 15.8 (q) |
| 26 | 1.03 (3H, d, 7.0) | 12.7 (q) |
| 27 | 0.90 (3H, d, 6.9) | 17.1 (q) |
| 28 | 0.96 (3H, d, 6.5) | 16.5 (q) |
| 29 | 1.65 (3H, s) | 23.4 (q) |
| 30 | 0.80 (3H, d, 6.6) | 13.1 (q) |
| 31 | 0.94 (3H, d, 6.3) | 8.7 (q) |
| 32 | 0.87 (3H, d, 7.3) | 15.7 (q) |
| 33 | — | 157.5 (s) |
| NH₂ | 4.70 (2H, br s) | — |

EXAMPLE 11

Preparation of 7-deoxy-8,21,23-hexahydrodiscodermolide-3,11,17-triacetate (XIV)

7-Deoxy-8,21,23-hexahydrodiscodermolide (2 mg) was dissolved in 0.5 mL of dry pyridine and treated with 2 μL of acetic anhydride. The mixture was stirred at room temperature overnight. The solvent was evaporated under a steam of nitrogen to give a white solid ~2 mg. The mixture was separated by HPLC using a SiO₂ semi-prep column (Phenomenex Luna column, 5μ, 250×10 mm) with 3% MeOH in CH₂Cl₂ as eluent to give pure 7-deoxy-8,21,23-hexahydrodiscodermolide-3,11,17-triacetate (1.5 mg). ¹H NMR data for this compound is shown in Table 10.

TABLE 10

¹H NMR Data for 7-Deoxy-8,21,23-hexahydrodiscodermolide-3,11,17-triacetate (XIV) CDCl₃, 500 MHz,

| Position | δ_H (mult., J in Hz) |
|---|---|
| 1 | — |
| 2 | 2.71 (1H, m) |
| 3 | 4.89 (1H, t, 3.6) |
| 4 | 2.05 (1H, overlapping m) |
| 5 | 4.28 (1H, dt, 7.2, 3.0) |
| 6 | 1.65, 1.50 (2H, overlapping m) |
| 7 | 1.30 (2H, overlapping m) |
| 8 | 1.40 (2H, overlapping m) |
| 9 | 1.32 (2H, overlapping m) |
| 10 | 1.65 (1H, overlapping m) |
| 11 | 4.63 (1H, dd, 8.0, 4.3) |
| 12 | 2.60 (1H, m) |
| 13 | 4.94 (1H, d, 10.1) |
| 14 | — |
| 15 | 1.63, 1.73 (2H, overlapping m) |
| 16 | 2.21 (1H, overlapping m) |
| 17 | 4.80 (1H, dd, 7.7. 4.2) |
| 18 | 2.07 (1H, overlapping m) |
| 19 | 4.56 (1H, dd, 7.9, 3.8) |
| 20 | 1.70 (1H, overlapping m) |
| 21 | 1.05, 1.15 (2H, overlapping m) |
| 22 | 1.35 (2H, overlapping m) |
| 23 | 1.25, 1.34 (2H, overlapping m) |
| 24 | 0.87 (3H, t, 6.7) |
| 25 | 1.31 (3H, d, 7.5) |
| 26 | 0.86 (3H, d, 6.5) |
| 27 | 0.81 (3H, d, 6.9) |
| 28 | 0.84 (3H, d, 6.7) |

TABLE 10-continued $^1$H NMR Data for 7-Deoxy-8,21,23-hexahydrodiscodermolide-3,11,17-triacetate (XIV) CDCl$_3$, 500 MHz.

| Position | $\delta_H$ (mult., J in Hz) |
|---|---|
| 29 | 1.63 (3H, s) |
| 30 | 0.72 (3H, d, 6.7) |
| 31 | 0.96 (3H, d, 6.7) |
| 32 | 0.85 (3H, d, 6.7) |
| 33 | — |
| Acetyl | 2.08 (3H, s) |
| Acetyl | 2.07 (3H, s) |
| Acetyl | 2.04 (3H, s) |

EXAMPLE 12

In vitro Antitumor Effects of Discodermolide and Discodermolide Analogs

A. Effects of Discodermolide and Analogs on In Vitro Proliferation of Tumor Cell Lines Discodermolide and discodermolide analogs were analyzed as to their effects on proliferation of A549 human adenocarcinoma and P388 murine leukemia cell lines. P388 cells were obtained from Dr. R. Camalier, National Cancer Institute, Bethesda, MD, and A549 cells were obtained from American Type Culture Collection, Rockville, MD. All cell lines were maintained in tissue culture medium (TCM; Roswell Park Memorial Institute RPMI 1640 supplemented with 100 U/mL penicillin, 100 mg/mL streptomycin, 60 mg/mL l-glutamine, 18 mM HEPES, 0.05 mg/mL gentamicin (Life Technologies, Gaithersburg, MD) and 10% fetal bovine serum) and cultured in plastic tissue culture flasks at 37° C. in humidified air containing 5% $CO_2$. Stock cultures of P388 cells were subcultured 1:20 in fresh TCM every 2 to 3 days. Stock cultures of A549 cells were subcultured 1:10 every 3 to 4 days. To assess the antiproliferative effects of agents against the cells, 200 µL cultures (96-well tissue culture plates, Nunc, Denmark) were established at 1 ×10$^5$ cells/mL in TCM or TCM containing the test agent at 0.03–5.0 µg/mL. After 48-h exposures, P388 cells were enumerated using 3-[4,5-dimethylthiazol-2-yl]-2,5-diphenyltetrazolium bromide (MTT) as described in the literature (M. C. Alley, et al., Cancer Res. 48:589, 1988). A549 cells were enumerated in the same manner after 72 hours exposure. The results were expressed as percent inhibition compared to the negative (no drug) control. Positive drug controls of varying dilutions of 5-fluorouracil and adriamycin (Sigma Chemical Co., St Louis, MO) were included to monitor drug sensitivity of the cell line.

To quantitate the effects on cell proliferation and resulting $IC_{50}$ values, 75 µL of warm growth media containing 5 mg/mL MTT is added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 µL of acidified isopropanol (2 mL concentrated HCl /liter isopropanol) added per well. The absorbance of the resulting solutions is measured in a plate reader (TECAN Spectra SLT; TECAN U.S., Research Triangle Park, N.C.) at 570 nm and a 650 nm reference filter. The absorbance of test wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp. 316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

A summary of results in these assays as compared to discodermolide (I) for compounds II–V can be found in Table 11. Results for compounds VI–XIV can be found in Table 12.

B. Effects of Discodermolide and Analogs on "Microtubule Bundling" Patterns in Tumor Cells as Detected by Immunofluorescence.

Discodermolide and discodermolide analogs were evaluated as to their effects on the morphology of the microtubule network of cells using mouse anti-alpha-tubulin monoclonal antibody. Cells treated with discodermolide routinely exhibit abnormal formation of multiple centriolar-radiating microtubules with extensive clusters of associated microtubular "bundles", unlike the fine "mesh" of individual microtubules which make up the cytoskeletal network in untreated control cells.

On day one, 7×10$^4$ adherent A549 human adenocarcinoma tumor cells were cultured in TCM overnight at 37° C. in 5% $CO_2$ on 22 mm$^2$ cover slips in 6-well microtiter plates. On day two, TCM was removed and replaced with 10–1000 nM discodermolide or analog in TCM or TCM without drug (control) and incubated overnight at 37° C. in 5% $CO_2$. On day three, TCM was removed and cells attached to cover slips were fixed with a 3.7% formaldehyde solution in Dulbecco's PBS for 10 minutes at room temperature. Cells were permeabilized with a 2% Triton X-100 solution, 2 mL per well, for 5 minutes at room temperature and washed twice in Dulbecco's PBS prior to staining.

To each well containing cells attached to cover slips a 2 mL volume of mouse anti- alpha-tubulin monoclonal antibody (Cat# T-5168, Sigma Chemical Co., St. Louis, Mo.) diluted 1:1000 in Dulbecco's phosphate buffered saline (D-PBS) was added and the cells incubated at room temperature for 45 minutes. Cover slips were rinsed once with D-PBS. A 2 mL volume of goat-anti-mouse-IgG-FITC conjugated antibody (Cat# T-5262, Sigma Chemical Co., St. Louis, Mo.) diluted 1:1000 in D-PBS was added and the cells incubated at room temperature for 45 minutes. Cover slips were rinsed once in D-PBS and DNA was stained with 0.02 mg/mL propidium iodide together with 0.1 mg/mL of ribonuclease A (RNAse) A in D-PBS at 37° C. for 30 minutes. Cover slips were rinsed three times with sterile distilled water, air-dried and mounted on slides with Slow-Fade™ antifade solution (Molecular Probes, Eugene, Oreg.) and observed under the microscope using epifluorescence illumination for the presence of abnormal aster and microtubule bundle formations.

A summary of the results in this assay as compared to discodermolide (I) for compounds II–V can be found in Table 11. Results for compounds VI–XIV can be found in Table 12.

C. Effect of Discodermolide and Analogs on Tubulin polymerization.

Polymerization of purified bovine brain tubulin (Cytoskeleton Inc., Denver, Colo.) was followed by changes in the optical density of tubulin solutions at 350 nm in a Hitachi U-3010 spectrophotometer equipped with a SPR-10 electronic thermostatted cell holder. Stock solutions of tubulin were diluted on ice in G-PEM buffer (1 mM GTP, 80 mM PIPES, 1 mM EGTA, 0.5 mM magnesium chloride; pH 6.8) to a final concentration of 1 mg/mL. The instrument was zeroed on this solution at 4° C. Discodermolide, and its analogs, were then added to the tubulin solution to a final concentration of 10 µM, quickly mixed, and the absorbance monitored over a period of 61 minutes. Within this time the temperature of the thermoelectric cell holder was held at 4°

C. for 1 minute, increased to 35° C. at a rate of 1° C./minute, reduced back to 4° C. at a rate of 2° C./minute, and held at 4° C. for an additional 14 minutes.

Figure 4:
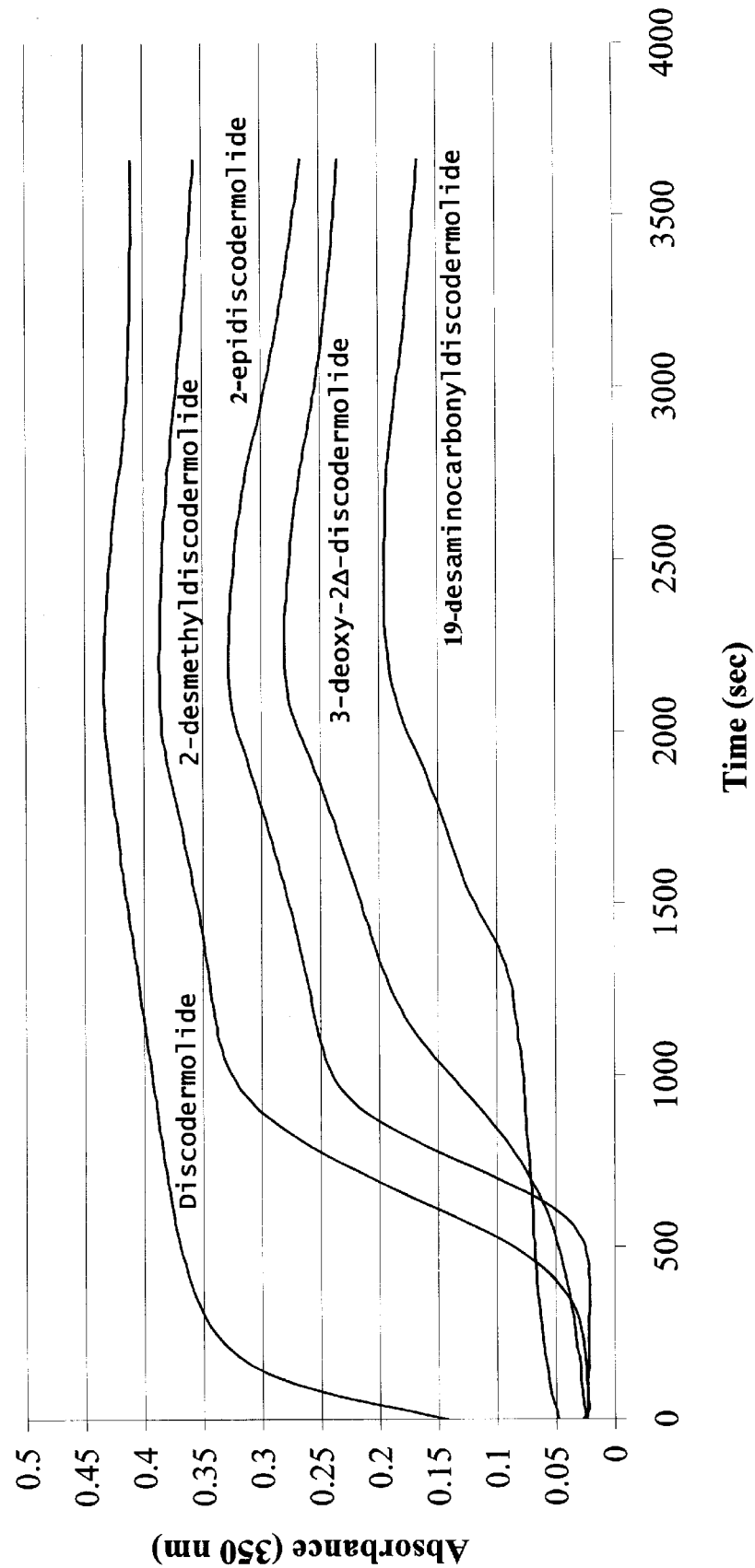
FIG. 4 shows induction of purified bovine brain tubulin polymerization as determined by monitoring the changes in optical density at 350 nm for 61 minutes. Compounds were tested at 10 $\mu$M with 1 mg/mL tubulin. The temperature was varied during the course of the experiment as follows: the experiment was begun with an initial temperature of 4° C. and held for 1 minute; the temperature was then increased to 35° C. at a rate of 1° C./minute, held at 35° C. for 1 minute, decreased to 4° C. at a rate of 2° C/minute, and finally held at 4° C. for 14 minutes. The curves shown are for compounds: discodermolide (I); 2-desmethyldiscodermolide (II); 19-desaminocarbonyldiscodermolide (III); 2-epidiscodermolide (IV); and 3-deoxy-2A-discodermolide (VI).
Figure 5:
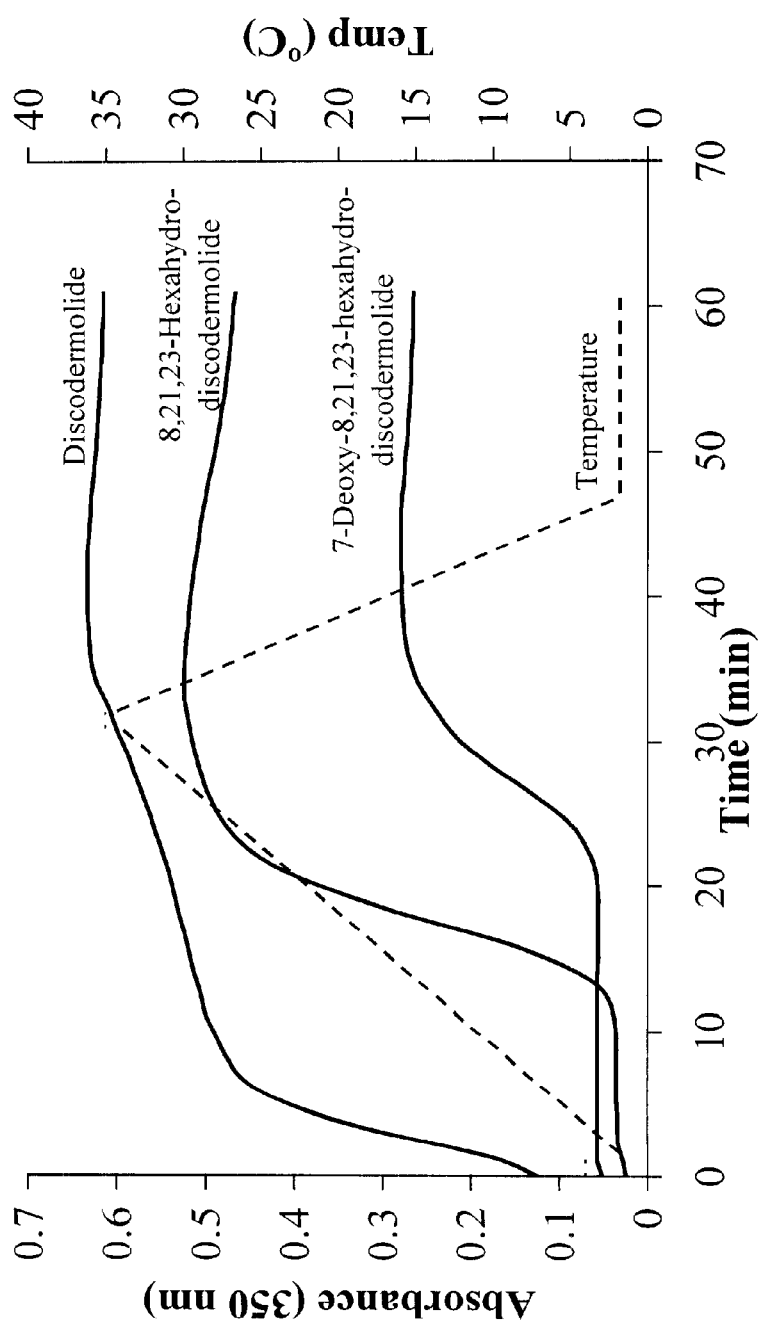
FIG. 5 shows induction of purified bovine brain tubulin polymerization as determined by monitoring the changes in optical density at 350 nm for 61 minutes. Compounds were tested at 10 $\mu$M with 1 mg/mL tubulin. The temperature was varied during the course of the experiment as follows: the experiment was begun with an initial temperature of 4° C. and held for 1 minute; the temperature was then increased to 35° C. at a rate of 1° C./minute, held at 35° C. for 1 minute, decreased to 4° C. at a rate of 2° C./minute, and finally held at 4° C. for 14 minutes. The curves shown are for discodermolide (I); 8,21,23-hexahydrodiscodermolide (XII) and 7-deoxy-8,21,23-hexahydrodiscodermolide (XIII).

A summary of the results in this assay as compared to discodermolide (I) for compounds II–V can be found in Table 11. Results for compounds VI–XIV can be found in Table 12. FIG. 4 shows the polymerization curves for compounds I–IV and VI. FIG. 5 shows the polymerization curves for compounds I, XII and XIII.

D. Effect of Discodermolide and Analogs on Cell Cycle Progression of A549 Human Lung Cells.

Cell cycle studies were initiated in order to pinpoint a specific phase within the cell cycle in which discodermolide analogs were exerting their antiproliferative effect. A549 human lung cells were used as cell cycle targets to compare the effects of discodermolide and discodermolide analogs on perturbation of the cell cycle. Cell cycle analyses were performed as follows: A549 cells were incubated at 37° C. in 5% $CO_2$ in air in the presence or absence of varying concentrations of discodermolide or discodermolide analogs for 24 hr. Cells were harvested, fixed in ethanol, washed, and stained with 0.02 mg/mL of propidium iodide (P.I.) together with 0.1 mg/mL of RNAse A. Stained preparations were analyzed on a Coulter EPICS ELITE flow cytometer with 488 nM excitation. Fluorescence measurements and resulting DNA histograms were collected from at least 10,000 P.I. stained cells at an emission wavelength of 690 nM. Raw histogram data was further analyzed using a cell cycle analysis program (Multicycle, Phoenix Flow Systems).

TABLE 11

Summary of Biological Activity of Discodermolide and Natural Analogs

| Compound (MW) | $IC_{50}$ = ng/mL or (nM) P388 cells | Micro- tubule bundling in A549 cells | Purified tubulin polymeri- zation by 10 $\mu$M (° C.) | Cell cycle effects (100 nM) |
|---|---|---|---|---|
| | A549 cells | | | |
| Discoder- molide (I) (593) | 21 (35) | 8 (13.5) | +++ | +++(4° C.) | $G_2/M$ block |
| 2-Des- methyl- discoder- molide (II) (581) | 100 (172) | 70 (120) | +++ | ++(10° C.) | Apopto- sis + $G_2/M$ block |
| 19-Des- amino- carbonyl discoder- molide (III) (546) | 70 (128) | 45 (74) | ++ | +(25° C.) | Strong apopto- sis + some $G_2/M$ block |
| 2-Epidis- codermolide (IV) (593) | 80 (134) | 40 (67) | + | ++(12° C.) | Strong apopto- sis + some $G_2/M$ block |
| Methyl- discoder- molate (V) (625) | 40 (65.8) | 45 (74) | + | (12° C.) | G2/M block |

Ratings for bundling and polymerization are subjective and are reported on the following scale in comparison to the effects of discodermolide: −no effect; +/−minimal or questionable effect; +weak effect; ++strong effect; +++very strong effect equivalent to discodermolide.

TABLE 12

Summary of Biological Activity of Semi-synthetic Analogs of Discodermolide.

| Compound (MW) | $IC_{50}$ = ng/mL or (nM) P388 cells | A549 cells | Micro- tubule bundl- ing in A549 cells | Purified tubulin polymeri- zation at 10 $\mu$M (° C.) | Cell cycle effects (100 nM) |
|---|---|---|---|---|---|
| 3-Deoxy-2Δ- discodermolide (VI) (575) | 20 (33.6) | 12.5 (21.7) | +++ | +(21° C.) | Some apopto- sis $G_2/M$ block |
| 3-Deoxy-2Δ- discodermolide- 17-acetate (VII) (617) | >5000 (>8103) | >5000 (>8103) | − | − | No effect |
| 3-Deoxy-2Δ- discodermolide- 11,17-diacetate (VIII) (659) | >5000 (>7587) | >5000 (>7587) | − | − | No effect |
| 3-Deoxy-2Δ- discodermolide- 7,11,17-triacetate (IX) (701) | 4960 (7076) | >5000 (>7133) | − | − | No effect |
| 3-Deoxy-2Δ- discodermolide- 11-acetate (X) (617) | 320 (519) | 1930 (3128) | − | − | No effect |
| 3-Deoxy-2Δ- discodermolide- 7-succinate (XI) (675) | >5000 (>7407) | Not run | − | Not run | No effect |
| 8,21,23- Hexahydro- discodermolide (XII) (599) | 20 (33.8) | 40 (67.7) | ++ | +++(16 C.) Some | apopto- sis and minor G2/M block |
| 7-Deoxy-8,21,23- hexahydrodis- codermolide (XIII)(583) | 180 (309) | 220 (377) | ++ | ++(24 C.) | No effect at 100 nM |
| 7-Deoxy-8,21,23- hexahydro- discodermolide- 3,11,17-triacetate (XIV) (709) | >5000 (>7502) | Not run | − | N/D | No effect |

Ratings for bundling and polymerization are subjective and are reported on the following scale in comparison to the effects of discodermolide: −no effect; +/−minimal or questionable effect; +weak effect; ++strong effect; +++very strong effect equivalent to discodermolide; N/D = not determined.

A summary of the results in this assay as compared to discodermolide (I) for compounds II–V can be found in Table 11. Results for compounds VI–XIV can be found in Table 12. FIGS. 6A–F show examples of the flow cytometric histograms observed for untreated control cells and compounds I, XII, XIII and XIV.

EXAMPLE 13

Biological Activity of 2-Desmethyldiscodermolide (II)

Microtubule Bundling in A549 Human Tumor Cells: At 1000 nM, the morphological changes were equivalent to those observed in cells exposed to 1000 nM discodermolide. There were fewer cells adhered than in the solvent control sample. The majority of cells were rounded with extensive microtubule bundling. Non-rounded cells showed that the majority of the microtubule matrix was condensed into perinuclear bundles. There was little polynucleation or morphological evidence of cells undergoing apoptosis. At 100 nM, the morphological effects seen were similar to those of cells exposed to 20–50 nM discodermolide. Some thin or short peripheral microtubule bundling was observed. Micronucleation characteristic of apoptosis was extensive and many cells had multiple aster formations. In addition many cells had a thin and elongated morphology that was not characteristic of discodermolide treatment.

Tubulin Polymerization:

This analog induced the polymerization of tubulin starting at approximately 9° C. The polymerized tubulin was stable at 4° C. This compound showed effects almost equivalent to those of the parent compound discodermolide since the addition of discodermolide caused only a small increase in the optical density.

Cell Cycle Effects:

This compound induced very strong apoptotic (sub-$G_1$ peak) effects as well as an increase in the percentage of cells residing in the $G_2$/M phase of the cell cycle.

These biological activities are summarized in Table 11.

EXAMPLE 14

Biological Activity of 19-Desaminocarbonyldiscodermolide (III)

Microtubule Bundling in A549 Human Tumor Cells:

At 1000 nM, there were fewer cells than in the negative control group. The majority of cells were rounded and lifting off of the surface and frequently had multiple aster formations. The remaining cells had a moderate amount of microtubule bundling which tended to be central and perinuclear in location. There was some polynucleation, as well as nuclear degradation indicative of apoptosis, but neither was extensive. The morphological changes were equivalent to those induced by 50–100 nM discodermolide. At 100 nM, there were more cells than in the 1000 nM group, but fewer than in the negative control. There was some microtubule bundling which tended to be peripheral, radiant, and frequently in shorter lengths than seen with 100 nM concentrations of discodermolide. Polynucleation as well as nuclear degradation indicative of apoptosis were both extensive through this population of cells. Cells with multiple aster formations were also readily found. The morphological changes were equivalent to those induced by 10–20 nM discodermolide.

Tubulin Polymerization:

This analog induced low levels of tubulin polymerization commencing at approximately 25° C. Maximum polymerization was only 30–50% that induced by discodermolide, and the polymers were relatively stable when the sample was held at 4° C.

Cell Cycle Effects:

Strong apoptosis; moderate $G_2$/M block.

These biological activities are summarized in Table 11.

EXAMPLE 15

Biological Activity of 2-Epidiscodermolide (IV)

Microtubule Bundling in A549 Human Tumor Cells:

At 1000 nM, the morphological changes to these cells was approximately equivalent to that of 20 nM discodermolide. Some minor, peripheral, polymerization of microtubule matrix was observed, but this was not extensive. Micronucleation characteristic of apoptosis was far greater than occurred in solvent control cells. There were a large number of cells with multiple aster formations. At 100 nM, the majority of cells look like the negative control sample. There was no microtubule matrix bundling and no observable changes in cellular distribution or morphology. A few cells were found with multiple aster formations, but this constituted less than 10% of the population undergoing mitosis. There was no noticeable increase in the occurrence of polynucleated cells or those with the morphological changes indicative of apoptosis.

Tubulin Polymerization:

This analog induced low levels of tubulin polymerization commencing at approximately 12° C. Maximum polymerization was only 30–50% that induced by discodermolide, and the polymers were relatively stable when the sample was held at 4° C.

Cell Cycle Effects:

Apoptosis and weak $G_2$/M block.

These biological activities are summarized in Table 11.

EXAMPLE 16

Biological Activity of 3-deoxy-2Δ-discodermolide-7-succinate (XI)

Microtubule Bundling in A549 Human Tumor Cells:

At 1000 nM, cells appeared flattened with single nuclei; microtubules were arranged in a fine mesh with no bundling, multiple asters or polynucleation. At 100 nM and 10 nM, the morphological appearance was indistinguishable from that of the untreated (control) cells.

Tubulin Polymerization:

Because of the similarity of the treated cells to that of the control, polymerization of purified tubulin was not tested.

Cell Cycle Effects:

At the highest concentration tested (3000 nM), no cell cycle effects were noted. There did appear to be a slight induction of apoptosis and a general necrosis indicated. At 1000 nM, 100 nM and 10 nM, the effects were indistinguishable from the untreated (control) cells.

These biological activities are summarized in Table 12.

EXAMPLE 17

Biological Activity of 82123-hexahydrodiscodermolide (XII)

Microtubule Bundling in A549 Human Tumor Cells:

There were fewer cells than in the control or discodermolide treated groups at both 1000 and 100 nM. Microtubule bundling was evident at both concentrations tested although it was not as extensive as discodermolide would be at these same concentrations. The majority of the cells were rounded and had multiple asters, or were in the mitotic phase of the cell cycle. Of the few cells that were adhered and spread, there did not appear to be a significant increase in micronucleation characteristic of apoptosis. Bundles that had formed were frequently curved along the periphery of the cells.

Tubulin Polymerization:

8,21,23-hexahydrodiscodermolide induced strong tubulin polymerization commencing at approximately 16° C. Maximum polymerization was approximately 80% of that induced by discodermolide, and the polymers were relatively stable when the sample was held at 4° C. This is shown in FIG. 5.

Figure 6A:
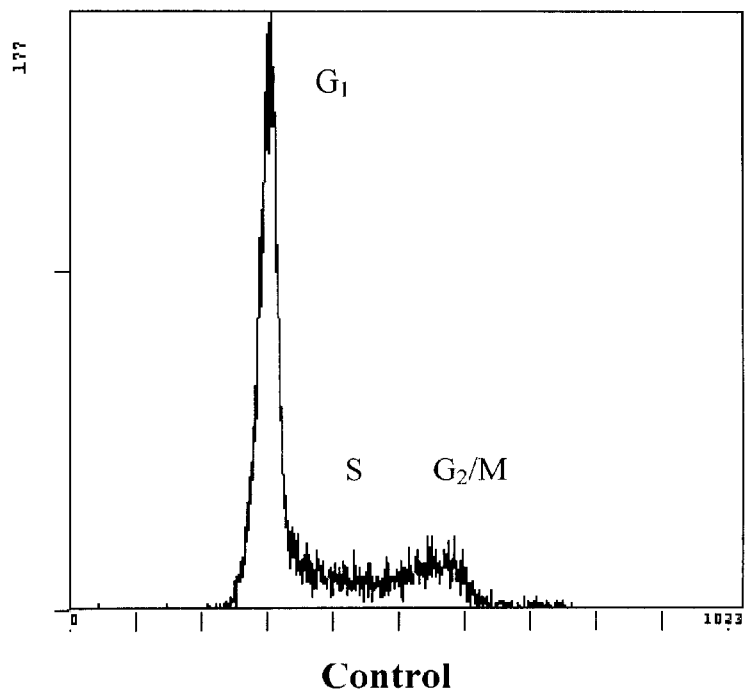
FIGS. 6A–F show flow cytometer histograms showing cell cycle effects on untreated vs. treated A549 human lung adenocarcinoma cells.
Figure 6B:
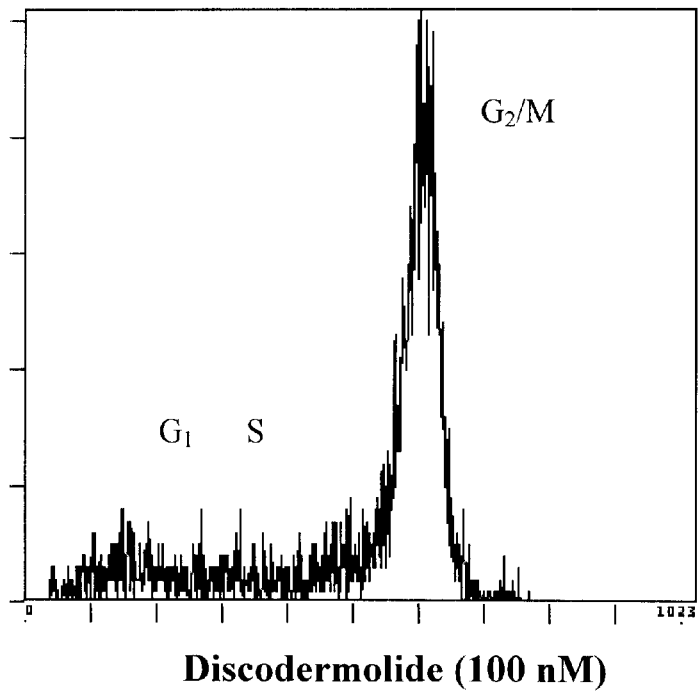
Figure 6C:
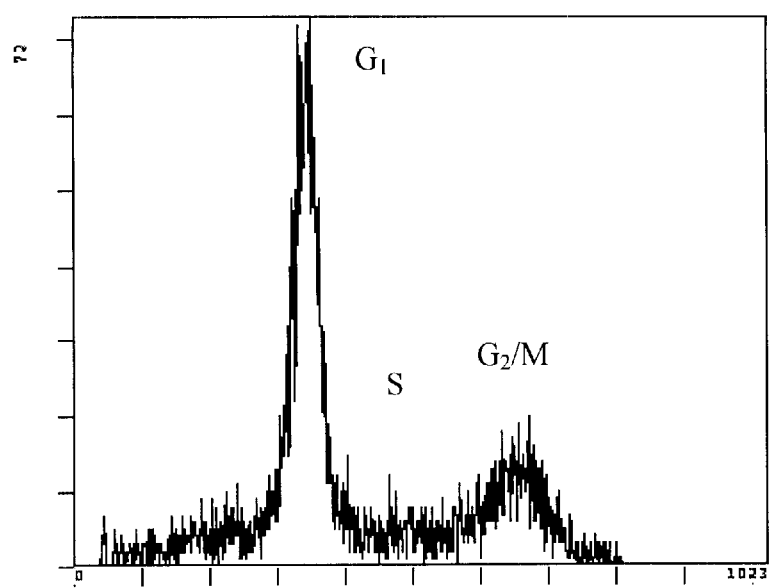

Cell Cycle Effects:

At 100 nM there was a small percent increase in the cells accumulated at the $G_2/M$ phase. This concentration induced a high percentage of apoptosis. This is shown in FIG. 6C.

These biological activities are summarized in Table 12.

EXAMPLE 18

Biological Activity of 7-deoxy-8,21,23-hexahydrodiscodermolide (XIII)

Microtubule Bundling in A549 Human Tumor Cells:

At 10 nM there was no visible effect on the microtubule matrix and only the occasional cell was seen with multiple aster formations. Cells exposed to 100 nM of the analog had effects comparable to cells exposed to 10 nM of discodermolide. A high percentage of M-phase cells had multiple aster formations, there was a small amount of microtubule bundling visible in some cells, and there was a high incidence of cells with nuclear degradation characteristic of apoptosis. Cells incubated with 1000 nM of the analog showed strong microtubule bundling equivalent to the morphological changes induced by 100 nM of discodermolide. There was ahigh percentage of cells undergoing apoptosis, as evident by nuclear degradation, and most rounded cells had multiple aster formations.

Tubulin Polymerization:

7-Deoxy-8,21,23-hexahydrodiscodermolide induced low levels of tubulin polymerization commencing at approximately 24° C. Maximum polymerization was 39% of that induced by discodermolide, and the polymers were relatively stable when the sample was held at 4° C. This is shown in FIG. 5.

Figure 6D:
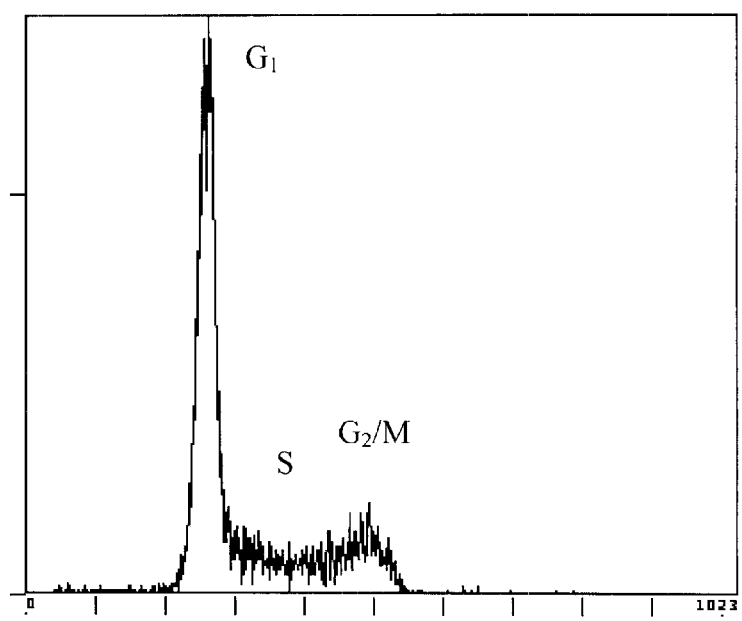
Figure 6E:
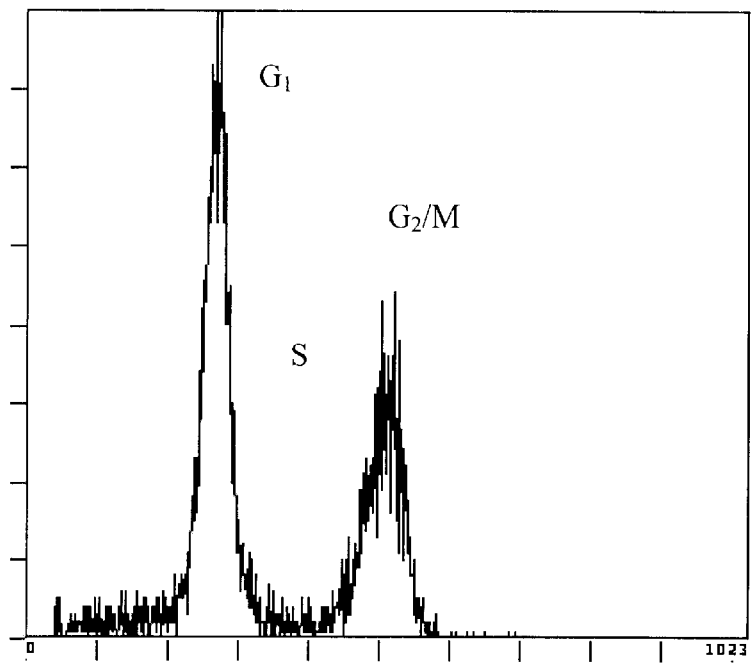

Cell Cycle Effects:

Approximately 50% of the cell population was accumulated in the $G_2/M$ phase following 24 hour incubation with 1000 nM 7-deoxy-8,21,23-hexahydrodiscodermolide. Lower concentrations did not produce any cell cycle effects. This is shown in FIGS. 6D and 6E.

These biological activities are summarized in Table 12.

EXAMPLE 19

Biological Activity of 7-deoxy-8,21,23-hexahydrodiscodermolide-3,11,17-triacetate (XIV)

Microtubule Bundling in A549 Human Tumor Cells:

At 10 nM through 1000 nM, the appearance of cells matched that of the no treatment/control cells; single nuclei centered in cell, microtubules were fine, distinctive and mesh-like; no bundling seen; no multiple asters; no apoptotic nuclei; no polynucleation.

Tubulin Polymerization:

Tubulin polymerization studies were not run on this compound, as it appeared to have no effect on any other parameters tested.

Figure 6F:
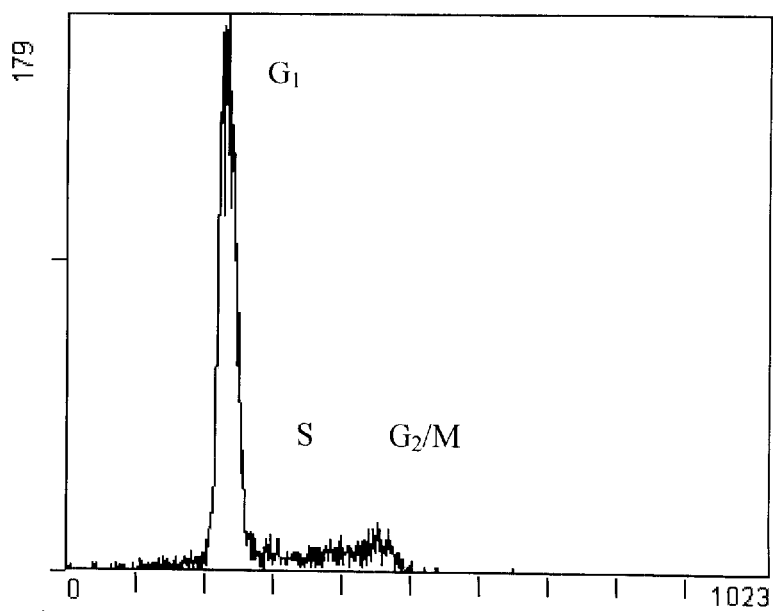

Cell Cycle Effects:

No cell cycle effects were noted at 10 nM, 100 nM or 1,000 nM. Percentage of cells in each phase of the cell cycle appeared to be similar to control (no treatment). This is shown in FIG. 6F.

These biological activities are summarized in Table 12.

EXAMPLE 20

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E.W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting the growth of cancer cells, said method comprising administering to said cells an effective amount of a discodermolide analog selected from the group consisting of 2-desmethyldiscodermolide (II);

19-desaminocarbonyldiscodermolide (III); methyldiscodermolate (V); 3-deoxy-2Δ-discodermolide (VI); 8,21,23-hexahydrodiscodermolide (XII); 7-deoxy-8,21,23-hexahydrodisco-dermolide (XIII); and derivatives of these compounds wherein said derivatives are not modified at the C-11 or C-17 positions.

2. The method, according to claim 1, wherein said analog is 2-desmethyldiscodermolide (II).

3. The method, according to claim 1, wherein said analog is 19-desaminocarbonyldiscodermolide (III).

4. The method, according to claim 1, wherein said analog is methyldiscodermolate (V).

5. The method, according to claim 1, wherein said analog is 3-deoxy-2Δ-discodermolide (VI).

6. The method, according to claim 1, wherein said analog is 8,21,23-hexahydrodiscodermolide (XII).

7. The method, according to claim 1, wherein said analog is 7-deoxy-8,21,23-hexahydrodiscodermolide (XIII).

8. The method, according to claim 1, wherein said cancer cells are selected from the group consisting of human leukemia, lung cancer, colon cancer, CNS cancer, melanoma, ovarian cancer, renal cancer, prostate cancer, breast cancer,liver cancer, pancreatic cancer, and uterine cancer.

9. A compound for inhibiting the growth of cancer cells, wherein said compound is selected from the group consisting of 2-desmethyldiscodermolide (II); 19-desaminocarbonyldiscodermolide (III); methyldiscodermolate (V); 3-deoxy-2Δ-discodermolide (VI); 8,21,23-hexahydrodiscodermolide (XII); 7-deoxy-8,21,23-hexahydrodiscodermolide (XIII); and derivatives of these compounds wherein said derivatives are not modified at the C-11 or C-17 positions.

10. The compound, according to claim 9, wherein said compound is 2-desmethyldiscodermolide (II).

11. The compound, according to claim 9, wherein said compound is 19-desaminocarbonyldiscodermolide (III).

12. The compound, according to claim 9, wherein said compound is methyldiscodermolate (V).

13. The compound, according to claim 9, wherein said compound is 3-deoxy-2Δ-discodermolide (VI).

14. The compound, according to claim 9, wherein said compound is 8,21,23-hexahydrodiscodermolide (XII).

15. The compound, according to claim 9, wherein said compound is 7-deoxy-8,21,23-hexahydrodiscodermilide (XIII).

16. A pharmaceutical composition a compound selected from the group consisting 2-desmethyldiscodermolide (II); 19-desaminocarbonyldiscodermolide (III); methyldiscodermolate (V); 3-deoxy-2Δ-discodermolide (VI); 8,21,23-hexahydrodiscodermolide (XII); 7-deoxy-8,21,23-hexahydrodisco-dermolide (XIII); and derivatives of these compounds wherein said derivatives are not modified at the C-11 or C-17 positions.

17. The pharmaceutical composition, according to claim 16, wherein said composition is 2-desmethyldiscodermolide (II).

18. The pharmaceutical composition, according to claim 16, wherein said composition is 19-desaminocarbonyldiscodermolide (III).

19. The pharmaceutical composition, according to claim 16, wherein said composition is methyldiscodermolate (V).

20. The pharmaceutical composition, according to claim 16, wherein said composition is 3-deoxy-2Δ-discodermolide (VI).

21. The pharmaceutical composition, according to claim 16, wherein said composition is 8,21,23-hexahydrodiscodermolide (XII).

22. The pharmaceutical composition, according to claim 16, wherein said composition is 7-deoxy-8,21,23-hexahydrodiscodermolide (XIII).

23. A discodermolide analog capable of inducing tubulin polymerization and stabilizing the microtubule network thus causing a block in the cell cycle at the G2/M checkpoint, wherein said analog is not functionalized at the C-11 or C-17 hydroxyl groups.

24. The discodermolide analog, according to claim 23, wherein said analog is modified, compared to natural discodermolide, along the C-1 to C-24 carbon backbone.

25. The discodermolide analog, according to claim 24, wherein said modification to the C-1 to C-24 carbon backbone comprises a modification selected from the group consisting of removal or addition of functionality, oxidation, reduction, lengthening, shortening, or cyclization.

26. The discodermolide analog, according to claim 25, wherein said modification to the C-1 to C-24 carbon backbone does not result in a significant modification of the spatial relationship between the C-11 and C-17 hydroxyl groups.

27. The discodermolide analog, according to claim 25, wherein said modification to the C-1 to C-24 carbon backbone does not result in a significant modification of the spatial relationship between the C-11 hydroxyl group, the C-17 hydroxyl group, and a C-21 to C-24 hydrophobic group.

28. The discodermolide analog, according to claim 25, wherein said modification to the C-1 to C-24 carbon backbone does not result in a significant modification of the spatial relationship between the C-11 hydroxyl group, the C-17 hydroxyl group, and a hydrogen bond acceptor.

29. The discodermolide analog, according to claim 28, wherein said hydrogen bond acceptor is a C-1 carbonyl or C-1 lactone functionality.

30. The discodermolide analog, according to claim 25, wherein said modification to the C-1 to C-24 carbon backbone does not result in a significant modification of the spatial relationship between the C-11 hydroxyl group, the C-17 hydroxyl group, and a C-21 to C-24 hydrophobic group, and a hydrogen bond acceptor.

31. The discodermolide analog, according to claim 30, wherein said hydrogen bond acceptor is a C-1 carbonyl or C-1 lactone functionality.

* * * * *

UNITED STATES PATENT AND TRADEMARK OFFICE
CERTIFICATE OF CORRECTION

PATENT NO.     : 6,495,594 B2
DATED          : December 17, 2002
INVENTOR(S)    : Sarath P. Gunasekera et al.

It is certified that error appears in the above-identified patent and that said Letters Patent is hereby corrected as shown below:

Column 2,
Line 13, "of (-) discodernolide" should read -- of (-) discodermolide --

Column 3,
Line 6, "regions ofthe" should read -- regions of the --
Line 66, "C-1 and C-17" should read -- C-11 and C-17 --

Column 4,
Line 19, "3-deoxy-2A-discodermolide" should read -- 3-deoxy-2Δ-discodermolide --
Line 44, "cells treated with 100 nM" should read -- cells treated with 1000 nM --

Column 6,
Line 16, "at theG2/m checkpoint" should read -- at the $G_2$/m checkpoint --
Line 17, "C-i through C-7" should read -- C-1 through C-7 --
Line 42, "HBOI CatNo." should read -- HBOI Cat No. --

Column 10,
Line 37, "3-deoxy-2A-discodermolide" should read -- 3-deoxy-2Δ-discodermolide --

Column 11,
Lines 34, 36, 42, 46 and 57, "3-deoxy-2A-discodermolide" should read -- 3-deoxy-2Δ-discodermolide --

Column 13,
Line 37, "3-deoxy-2A-discodermolide" should read -- 3-deoxy-2Δ-discodermolide --
Line 65, "the residue on cation" should read -- the residue on purification --

Column 14,
Line 7, "C-1" should read -- C-11 --

Column 16,
Line 56, "hexahydrodiscodernolide" should read -- hexahydrodiscodermolide --
Line 60, "Discodernolide (34.0 mg)" should read -- Discodermolide (34.0 mg) --

Column 21,
Line 59, "G2/m block" should read -- $G_2$/m block --

UNITED STATES PATENT AND TRADEMARK OFFICE
CERTIFICATE OF CORRECTION

PATENT NO. : 6,495,594 B2
DATED : December 17, 2002
INVENTOR(S) : Sarath P. Gunasekera et al.

It is certified that error appears in the above-identified patent and that said Letters Patent is hereby corrected as shown below:

Column 22,
Line 37, "G2/m block" should read -- $G_2$/m block --

Column 28,
Line 17, "G2/m checkpoint" should read -- $G_2$/m checkpoint --

Signed and Sealed this

Seventh Day of October, 2003

JAMES E. ROGAN
*Director of the United States Patent and Trademark Office*